(12) United States Patent
Murali et al.

(10) Patent No.: US 10,881,641 B2
(45) Date of Patent: Jan. 5, 2021

(54) METHODS AND USE OF COMPOUNDS THAT BIND TO RELA OF NF-KB

(71) Applicant: Cedars-Sinai Medical Center, Los Angeles, CA (US)

(72) Inventors: Ramachandran Murali, Beverly Hills, CA (US); Hirotaka Kanzaki, Okayama (JP)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 0 days.

(21) Appl. No.: 15/828,097

(22) Filed: Nov. 30, 2017

(65) Prior Publication Data

US 2018/0078528 A1    Mar. 22, 2018

Related U.S. Application Data

(63) Continuation of application No. PCT/US2016/035318, filed on Jun. 1, 2016.

(60) Provisional application No. 62/169,466, filed on Jun. 1, 2015.

(51) Int. Cl.
| | | |
|---|---|---|
| A61K 31/4174 | (2006.01) |
| A61P 35/00 | (2006.01) |
| A61K 31/04 | (2006.01) |
| A61K 31/10 | (2006.01) |
| A61K 31/403 | (2006.01) |
| A61K 31/4164 | (2006.01) |
| A61K 31/428 | (2006.01) |
| A61K 31/445 | (2006.01) |
| A61K 31/495 | (2006.01) |
| A61K 31/5375 | (2006.01) |

(52) U.S. Cl.
CPC .......... *A61K 31/4174* (2013.01); *A61K 31/04* (2013.01); *A61K 31/10* (2013.01); *A61K 31/403* (2013.01); *A61K 31/4164* (2013.01); *A61K 31/428* (2013.01); *A61K 31/445* (2013.01); *A61K 31/495* (2013.01); *A61K 31/5375* (2013.01); *A61P 35/00* (2018.01)

(58) Field of Classification Search
None
See application file for complete search history.

(56) References Cited

U.S. PATENT DOCUMENTS

2005/0124590 A1    6/2005 Kuwada

FOREIGN PATENT DOCUMENTS

WO    2013112601 A1    8/2013

OTHER PUBLICATIONS

National Center for Biotechnology Information. PubChem Substance Database; SID=271228478, https://pubchem.ncbi.nlm.nih.gov/substance/271228478 (accessed Nov. 22, 2017).

*Primary Examiner* — Kortney L. Klinkel
*Assistant Examiner* — Tori Strong
(74) *Attorney, Agent, or Firm* — Nixon & Vanderhye P.C.

(57) ABSTRACT

The invention provides methods and agents that modulate RelA activity. These methods and modulators of RelA activity can be used to treat cancer progression of basal-like breast cancer, such as triple-negative breast cancer.

13 Claims, 2 Drawing Sheets

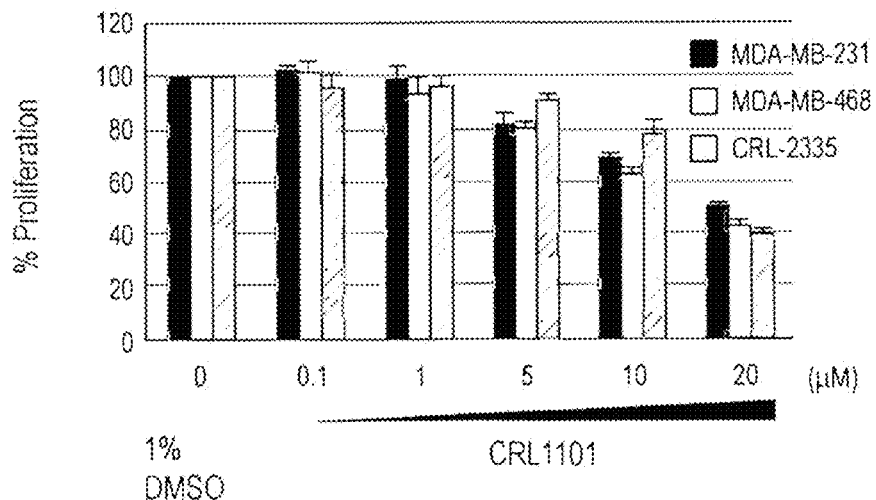
[FIG. 1A]
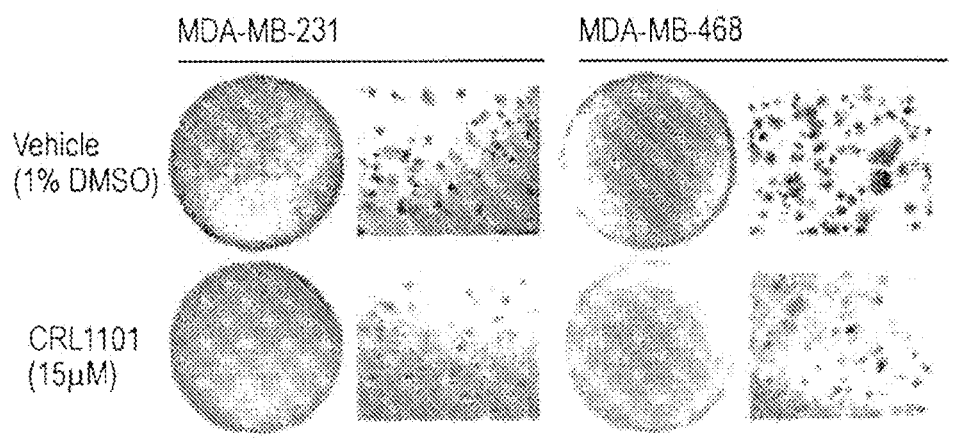
[FIG. 1B]

[FIG. 2]
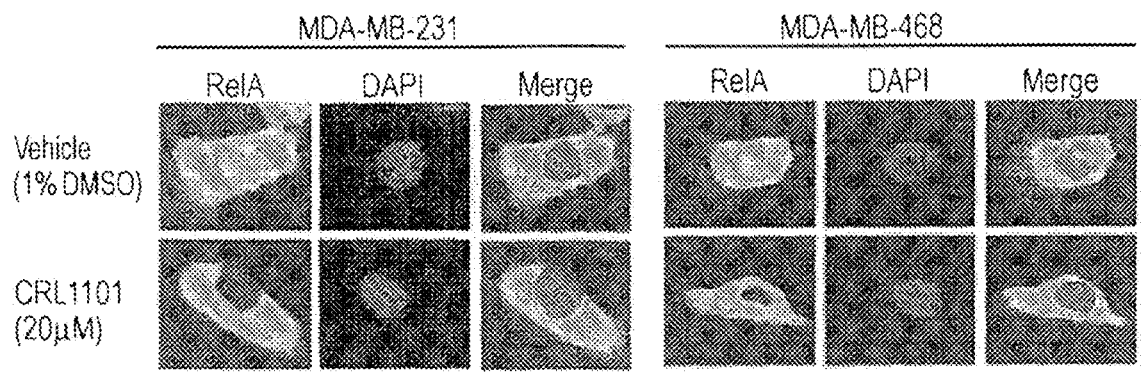
[FIG. 3]
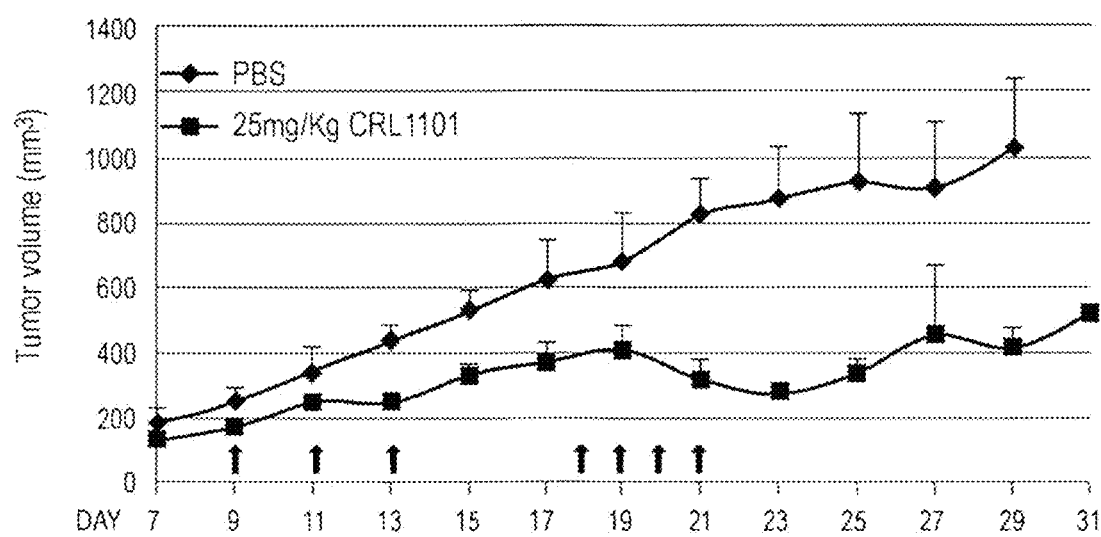

METHODS AND USE OF COMPOUNDS THAT BIND TO RELA OF NF-KB

CROSS REFERENCE TO RELATED APPLICATIONS

This claims benefit under 35 U.S.C. § 119(e) of U.S. Provisional Patent Application Ser. No. 61/169,466 filed on Jun. 1, 2015, content of which is incorporated herein by reference in its entirety.

TECHNICAL FIELD

The present disclosure relates generally to blocking p65/RelA function of NF-kB, which prevents cancer progression of basal-like breast cancer, such as triple-negative breast cancer.

BACKGROUND

Chemotherapy is the standard treatment for patients with Triple-negative breast cancer (TNBC). Although it improves the prognosis, about 30% of the patients die due to resistance to therapy and metastasis. There are no targeted therapies to improve these patients. NF-kB is constitutively activated in several cancers including triple-negative breast cancer, and is responsible for resistance to therapy. This invention constitutes a new targeted therapy for cancer, including but not limited to TNBC.

SUMMARY

Various aspects of the invention disclosed herein are based on inventors' discovery of molecules that can block RelA transport from cytoplasm into nucleus and thereby alter gene-expression profiles. Accordingly, described herein are methods and molecules for modulating, including but not limited to inhibiting, reducing and/or decreasing, binding and/or function of RelA mediated gene expression. In the various aspects describe herein, a compound that modulates the binding and function of RelA can be of Formula I:

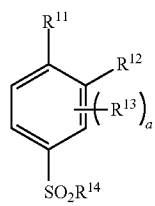

Formula I wherein:
a is 0, 1, 2 or 3;
$R^{11}$ and $R^{12}$ can be same or different, and are independently hydrogen, alkyl, alkenyl, alkynyl, halogen, aryl, heteroaryl, cyclyl, heterocyclyl, carbonyl, carboxy, cyano, hydroxyl, alkoxy, aroxy, nitro, aralkyl, sulfinyl, sulfonyl, thiocabonyl, thio, alkylthio, arylthio, amino, aminoalkyl, mono- or di-alkylamino, arylamino, heteroarylamino or $CF_3$, each of which can be optionally substituted;
$R^{13}$ is independently for each occurrence alkyl, alkenyl, alkynyl, halogen, aryl, heteroaryl, cyclyl, heterocyclyl, carbonyl, carboxy, cyano, hydroxyl, alkoxy, aroxy, nitro, aralkyl, sulfinyl, sulfonyl, thiocabonyl, thio, alkylthio, arylthio, amino, aminoalkyl, mono- or di-alkylamino, arylamino, heteroarylamino or $CF_3$, each of which can be optionally substituted;
$R^{14}$ is hydrogen, alkyl, alkenyl, alkynyl, halogen, aryl, heteroaryl, cyclyl, heterocyclyl, carbonyl, carboxy, cyano, hydroxyl, alkoxy, aroxy, nitro, aralkyl, sulfinyl, sulfonyl, thiocabonyl, thio, alkylthio, arylthio, amino, aminoalkyl, mono- or di-alkylamino, arylamino, heteroarylamino or $CF_3$, each of which can be optionally substituted; and
stereoisomers and pharmaceutically acceptable salts thereof.

In the various aspects describe herein, a compound that blocks or modulate RelA/p65 function can be of Formula II:

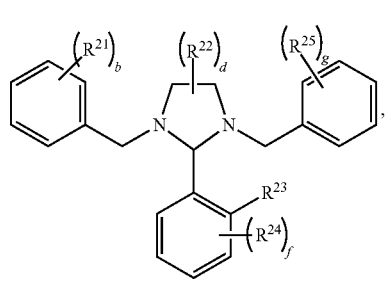

Formula II wherein:
b and g can be same or different and are independently 0, 1, 2, 3, 4 or 5;
d is 0, 1 or 2;
f is 0, 1, 2, 3 or 4;
$R^{21}$, $R^{24}$ and $R^{25}$ can be all same or all different or two same and one different, and independently for each occurrence hydrogen, alkyl, alkenyl, alkynyl, halogen, aryl, heteroaryl, cyclyl, heterocyclyl, carbonyl, carboxy, cyano, hydroxyl, alkoxy, aroxy, nitro, aralkyl, sulfinyl, sulfonyl, thiocabonyl, thio, alkylthio, arylthio, amino, aminoalkyl, mono- or di-alkylamino, arylamino, heteroarylamino or $CF_3$, each of which can be optionally substituted;
$R^{22}$ is independently for each occurrence alkyl, alkenyl, alkynyl, halogen, aryl, heteroaryl, cyclyl, heterocyclyl, carbonyl, carboxy, cyano, hydroxyl, alkoxy, aroxy, nitro, aralkyl, sulfinyl, sulfonyl, thiocabonyl, thio, alkylthio, arylthio, amino, aminoalkyl, mono- or di-alkylamino, arylamino, heteroarylamino or $CF_3$, each of which can be optionally substituted, or two $R^{22}$ together with the carbon atoms they are attached to form an optionally substituted 5-8 membered cyclyl, heterocylyl, aryl or heteroaryl;
$R^{23}$ is hydrogen, alkyl, alkenyl, alkynyl, halogen, aryl, heteroaryl, cyclyl, heterocyclyl, carbonyl, carboxy, cyano, hydroxyl, alkoxy, aroxy, nitro, aralkyl, sulfinyl, sulfonyl, thiocabonyl, thio, alkylthio, arylthio, amino, aminoalkyl, mono- or di-alkylamino, arylamino, heteroarylamino or $CF_3$, each of which can be optionally substituted; and
stereoisomers and pharmaceutically acceptable salts thereof.

In the various aspects describe herein, a compound that blocks or modulate RelA/p65 function can be of Formula III:

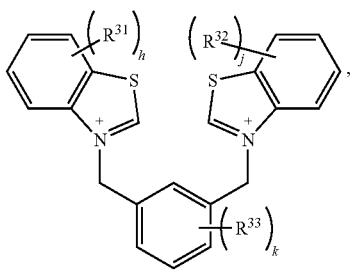

Formula III wherein:
h is 0, 1, 2, 3 or 4;
j is 0, 1, 2, 3 or 4;
k is 0, 1, 2, 3 or 4;
$R^{31}$, $R^{32}$ and $R^{33}$ can all be same or all different or two are same, and are independently for each occurrence alkyl, alkenyl, alkynyl, halogen, aryl, heteroaryl, cyclyl, heterocyclyl, carbonyl, carboxy, cyano, hydroxyl, alkoxy, aroxy, nitro, aralkyl, sulfinyl, sulfonyl, thiocabonyl, thio, alkylthio, arylthio, amino, aminoalkyl, mono- or di-alkylamino, arylamino, heteroarylamino or $CF_3$, each of which can be optionally substituted; and stereoisomers and pharmaceutically acceptable salts thereof.

In the various aspects describe herein, a compound that blocks or modulate RelA/p65 function can be of Formula IV:

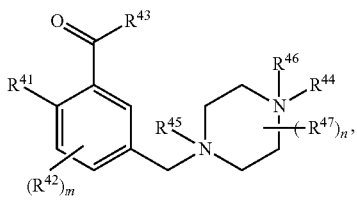

Formula IV wherein:
m is 0, 1, 2, or 3;
n is 0, 1, 2, 3 or 4;
$R^{41}$ is hydrogen, alkyl, alkenyl, alkynyl, halogen, aryl, heteroaryl, cyclyl, heterocyclyl, carbonyl, carboxy, cyano, hydroxyl, alkoxy, aroxy, nitro, aralkyl, sulfinyl, sulfonyl, thiocabonyl, thio, alkylthio, arylthio, amino, aminoalkyl, mono- or di-alkylamino, arylamino, heteroarylamino or $CF_3$, each of which can be optionally substituted;
$R^{42}$ is independently for each occurrence alkyl, alkenyl, alkynyl, halogen, aryl, heteroaryl, cyclyl, heterocyclyl, carbonyl, carboxy, cyano, hydroxyl, alkoxy, aroxy, nitro, aralkyl, sulfinyl, sulfonyl, thiocabonyl, thio, alkylthio, arylthio, amino, aminoalkyl, mono- or di-alkylamino, arylamino, heteroarylamino or $CF_3$, each of which can be optionally substituted;
$R^{43}$ is hydrogen, alkyl, alkenyl, alkynyl, aryl, heteroaryl, cyclyl, heterocyclyl, hydroxyl, alkoxy, aroxy, nitro, aralkyl, sulfinyl, sulfonyl, thiocabonyl, thio, alkylthio, arylthio, amino, aminoalkyl, mono- or di-alkylamino, arylamino, heteroarylamino or $CF_3$, each of which can be optionally substituted;
$R^{44}$, $R^{45}$ and $R^{46}$ can be same or different, and are independently for each occurrence absent, hydrogen, alkyl, alkenyl, alkynyl, aryl, heteroaryl, cyclyl, hetero-cyclyl, aralkyl, sulfinyl, sulfonyl, carbonyl, carboxy, thiocabonyl, thio, alkylthio, arylthio or $CF_3$, each of which can be optionally substituted, provided that at least one of $R^{44}$ and $R^{46}$ is not absent;
$R^{47}$ is independently for each occurrence alkyl, alkenyl, alkynyl, halogen, aryl, heteroaryl, cyclyl, heterocyclyl, carbonyl, carboxy, cyano, hydroxyl, alkoxy, aroxy, nitro, aralkyl, sulfinyl, sulfonyl, thiocabonyl, thio, alkylthio, arylthio, amino, aminoalkyl, mono- or di-alkylamino, arylamino, heteroarylamino or $CF_3$, each of which can be optionally substituted; and stereoisomers and pharmaceutically acceptable salts thereof.

In the various aspects describe herein, a compound that modulates the binding and function of RelA can be of Formula V:

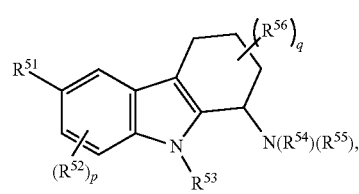

Formula V wherein:
p and q are same or different and are independently 0, 1, 2, or 3;
$R^{51}$ is hydrogen, alkyl, alkenyl, alkynyl, halogen, aryl, heteroaryl, cyclyl, heterocyclyl, carbonyl, carboxy, cyano, hydroxyl, alkoxy, aroxy, nitro, aralkyl, sulfinyl, sulfonyl, thiocabonyl, thio, alkylthio, arylthio, amino, aminoalkyl, mono- or di-alkylamino, arylamino, heteroarylamino or $CF_3$, each of which can be optionally substituted;
$R^{52}$ is independently for each occurrence alkyl, alkenyl, alkynyl, halogen, aryl, heteroaryl, cyclyl, heterocyclyl, carbonyl, carboxy, cyano, hydroxyl, alkoxy, aroxy, nitro, aralkyl, sulfinyl, sulfonyl, thiocabonyl, thio, alkylthio, arylthio, amino, aminoalkyl, mono- or di-alkylamino, arylamino, heteroarylamino or $CF_3$, each of which can be optionally substituted;
$R^{53}$, $R^{54}$ and $R^{55}$ can be all same, all different or two are same, and are independently for each occurrence hydrogen, alkyl, alkenyl, alkynyl, aryl, heteroaryl, cyclyl, heterocyclyl, aralkyl, sulfinyl, sulfonyl, carbonyl, carboxy, thiocabonyl, thio, alkylthio, arylthio or $CF_3$, each of which can be optionally substituted;
$R^{56}$ is independently for each occurrence alkyl, alkenyl, alkynyl, halogen, aryl, heteroaryl, cyclyl, heterocyclyl, carbonyl, carboxy, cyano, hydroxyl, alkoxy, aroxy, nitro, aralkyl, sulfinyl, sulfonyl, thiocabonyl, thio, alkylthio, arylthio, amino, aminoalkyl, mono- or di-alkylamino, arylamino, heteroarylamino or $CF_3$, each of which can be optionally substituted; and stereoisomers and pharmaceutically acceptable salts thereof.

It is noted that the carbon to which $N(R^{54})(R^{56})$ is attached can be in the R or S configuration. Accordingly, in some embodiments, the carbon to which $N(R^{54})(R^{56})$ is attached in the R configuration. In some other embodiments, the carbon to which $N(R^{54})(R^{56})$ is attached in the S configuration.

In some embodiments of the various aspects described herein, the compound that modulates the binding and/or function of RelA and blocks nuclear translocalization is selected from the group consisting of CRL1101, having the structure:

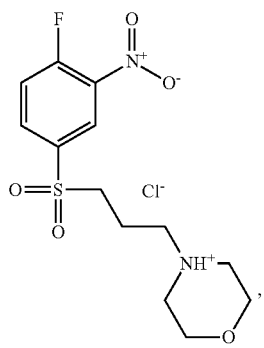 [SMILES: O=[N+]([O-])c1cc(S(=O)(=O)CCC[NH+]2CCOCC2)ccc1F ; [Cl-]]

CRL1102, having the structure:

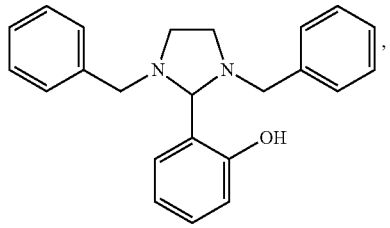 [SMILES: Oc1ccccc1C1N(Cc2ccccc2)CCN1Cc1ccccc1]

CRL11021, having the structure:

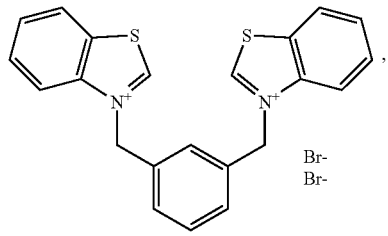 [SMILES: c1cc(C[n+]2csc3ccccc32)cc(C[n+]2csc3ccccc32)c1]

CRL1103, having the structure:

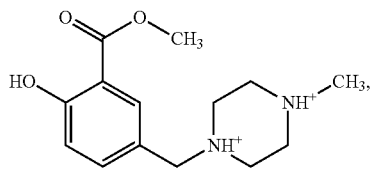

CRL1104, having the structure:

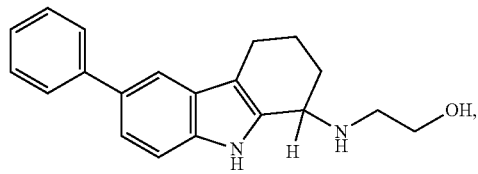 [SMILES: OCCNC1CCCc2c1[nH]c1ccc(-c3ccccc3)cc21]

and CRL11041, having the structure:

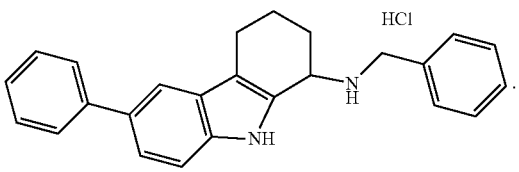 [SMILES: c1ccc(CNC2CCCc3c2[nH]c2ccc(-c4ccccc4)cc32)cc1 ; Cl]

In some aspects, described herein are methods of modulating binding and/or function of RelA blocks nuclear translocation. The method generally comprising contacting a compound of Formula I, II, III, IV or V with the RelA.

In some aspects, described herein are methods of modulating, e.g., inhibiting or reducing or decreasing, binding and/or function of RelA blocks nuclear translocation in a subject in need thereof. Such methods comprise administering to a subject a therapeutically effective amount of a compound of Formula, I, II, III, IV or V.

In other aspects, described herein are methods of treating, inhibiting, reducing severity of, slowing progression of and/or preventing metastasis of a cancer or a cancerous condition by modulating RelA activity. Such methods comprise administering to a subject having a cancer or cancerous condition a therapeutically effective amount of a compound of Formula I, II, III, IV or V described herein.

In some embodiments of the various aspects described herein, the methods further comprise the step of selecting the subject having a cancer, a cancerous condition, or a tumor.

In some embodiments of these methods, the cancer is a breast cancer, squamous cell cancer, lung cancer, a cancer of the peritoneum, a hepatocellular cancer, a gastric cancer, a pancreatic cancer, a glioblastoma, a cervical cancer, an ovarian cancer, a liver cancer, a bladder cancer, a hepatoma, a colon cancer, a colorectal cancer, an endometrial or uterine carcinoma, a salivary gland carcinoma, a kidney or renal cancer, a prostate cancer, a vulval cancer, a thyroid cancer, a head and neck cancer, a B-cell lymphoma, a chronic lymphocytic leukemia (CLL); an acute lymphoblastic leukemia (ALL), a Hairy cell leukemia, or a chronic myeloblastic leukemia. In some such embodiments, the cancer is a breast cancer. In some embodiments, the cancer is triple negative breast cancer.

Some embodiments of these methods can further comprise administration or treatment with one or more additional anti-cancer therapies. In some such embodiments, the additional anti-cancer therapy comprises surgery, radiation therapy, biotherapy, immunotherapy, chemotherapy, or any combination thereof.

Some embodiments of these methods can further comprise administration or treatment with one or more anti-cancer therapeutic agents. In some such embodiments, the anti-cancer therapeutic agent is a chemotherapeutic agent, a growth inhibitor agent, an anti-angiogenesis agent, a cytotoxic agent, an anti-hormonal agent, a prodrug, or a cytokine.

Also provided herein are pharmaceutical compositions comprising a compound of Formula I, II, III, IV or V, and a pharmaceutically acceptable excipient or carrier. Such pharmaceutical composition can be used for blocking RelA/p65 function in a subject in need thereof.

In some aspects, pharmaceutical compositions comprising a compound of Formula I, II, III, IV or V are provided for use in treating, inhibiting, reducing severity of, slowing progression of and/or preventing metastasis of a cancer or a cancerous condition by blocking or modulating RelA/p65 function or activity.

In some embodiments of these aspects and all such aspects described herein, the use further comprises the step of selecting the subject having a cancer, a cancerous condition, or a tumor. In some such embodiments, the cancer is a breast cancer, squamous cell cancer, lung cancer, a cancer of the peritoneum, a hepatocellular cancer, a gastric cancer, a pancreatic cancer, a glioblastoma, a cervical cancer, an ovarian cancer, a liver cancer, a bladder cancer, a hepatoma, a colon cancer, a colorectal cancer, an endometrial or uterine carcinoma, a salivary gland carcinoma, a kidney or renal cancer, a prostate cancer, a vulval cancer, a thyroid cancer, a head and neck cancer, a B-cell lymphoma, a chronic lymphocytic leukemia (CLL); an acute lymphoblastic leukemia (ALL), a Hairy cell leukemia, or a chronic myeloblastic leukemia. In some such embodiments, the cancer is a breast cancer.

In some embodiments of these aspects and all such aspects described herein, the use further comprises one or more additional anti-cancer therapies. In some such embodiments, the additional anti-cancer therapy comprises surgery, radiation therapy, biotherapy, immunotherapy, or chemotherapy.

In some embodiments of these aspects and all such aspects described herein, the use further comprises one or more anti-cancer therapeutic agents. In some such embodiments, the anti-cancer therapeutic agent is a chemotherapeutic agent, a growth inhibitor agent, an anti-angiogenesis agent, a cytotoxic agent, an anti-hormonal agent, a prodrug, or a cytokine.

BRIEF DESCRIPTION OF THE DRAWINGS

FIG. 1A shows TNBC Biological activity of CRL1101 in triple-negative breast cancer cell lines. CRL1011 significantly (IC50=20, uM) inhibited all the three TNBC cell line proliferation as measured by calorimetric assay (MTT).

FIG. 1B shows the inhibition of tumor growth by anchorage independent growth assay. The effects of CRL1101 on clonogenic survival were analyzed. Base layers consisting of growth medium containing 0.53% low-melting point agarose (Invitrogen) were poured onto 6-well plates and allowed to solidify. Cells were seeded at concentration of 10000/well in triplicate in top layers consisting of growth medium containing 0.32% agarose. After 24 hours, 15, uM of CRL1101 was added. Cells were incubated for 14 days to form visible colonies. The colonies were fixed and stained by 0.05% Crystal violet in 50% methanol.

FIG. 2 shows the nuclear localization of RelA in TNBC cell lines by Immunofluorescent staining. Cells were grown in Dulbecco's modified Eagle medium supplemented with 10% heat-inactivated fetal calf serum and 1% (w/v) penicillin/streptomycin (all purchased from Mediatech Inc, Manassas, Va., USA). Cells were treated with or without 20 mM of CRL1101 in 1% DMSO. Forty five minutes after treatment, cells were fixed with 4% formaldehyde for 10 min and sequentially treated with 0.1% Triton X 100 for 10 min. Cells were blocked in 1% BSA in PBS for 10 min. cells were incubated with anti-Re/A(p65) antibody (1:150, Abeam, Cambridge, UK) in PBS with 1% BSA overnight at 4° C. and a secondary antibody (1:1000 anti-rabbit Alexa 488, Invitrogen, Carlsbad, Calif., USA) for 1 hr in the dark. Analyses were performed using a microscope (Nikon ECLIPSE Ti-U, Nikon, Tokyo, JAPAN). Green signal shows RelA(p65), blue signal shows DAPI.

FIG. 3 shows tumor growth mediated by MD-MBA-231 cells assessed in athymic mice. Mice were administrated 25 mg/kg/day of CRL1101 or vehicle IP, as indicated by arrows. Results are given as mean tumor volume +− s.e. Tumor growth in animals treated with CRL1101 was significant ($p<0.001$) compared to vehicle. N=6.

DETAILED DESCRIPTION

Described herein are compounds, compositions and methods that modulate or block RelA/p65 function or activity. The inventors have discovered small molecule compounds of Formula I, II, III, IV and V that modulate RelA nuclear translocalization and can be used to treat and inhibit proliferative disorders and metastasis such as cancer.

RelA, also known as p65, is a REL-associated protein involved in NF-κB heterodimer formation, nuclear translocation and activation. NF-κB is an essential transcription factor complex involved in all types of cellular processes, including cellular metabolism, chemotaxis, etc. Phosphorylation and acetylation of RELA are crucial post-translational modifications required for NF-κB activation. RELA has also been shown to modulate immune responses, and activation of RELA in the nucleus is positively associated with multiple types of cancer.

As the prototypical heterodimer complex member of the NF-κB, together with p50, RELA/p65 interacts with various proteins in both the cytoplasm and in the nucleus during the process of classical NF-κB activation and nuclear translocation. In the inactive state, RELA/p50 complex is mainly sequestered by 3a in the cytosol. TNFα, LPS and other factors serve as activation inducers, followed by phosphorylation at residue 32 and 36 of IκBα, leading to rapid degradation of 3a via the ubiquitin-proteasomal system and subsequent release of RELA/p50 complex. RELA nuclear localization signal used to be sequestered by 3a is now exposed, and rapid translocation of the NF-κB occurs. After NF-κB nuclear localization due to TNF stimulation, p50/RELA heterodimer can function as a transcription factor and bind to a variety of genes involved in all kinds of biological processes, such as leukocyte activation/chemotaxis, negative regulation of TNF/IKK pathway, cellular metabolism, antigen processing, just to name a few. Phosphorylation of RELA at different residues also enables its interaction with CDKs and P-TEFb. Phosphorylation at serine 276 in RELA allows its interaction with P-TEFb containing CDK-9 and cyclin T1 subunits, and phospho-ser276 RELA-P-TEFb complex is necessary for IL-8 and Gro-β activation. Another mechanism is involved in the activation of genes preloaded with Pol II in a RELA ser 276 phosphorylation independent manner.

NF-κB/RELA activation has been found to be correlated with cancer development, suggesting the potential of RELA as a cancer biomarker. Specific modification patterns of RELA have also been observed in many cancer types. There is both a physical and a functional association between RELA and aryl hydrocarbon receptor (AhR), and the subsequent activation of c-myc gene transcription in breast cancer cells. Prior art has also reported interactions between estrogen receptor(ER) and NF-κB members, including p50 and RELA. It has been shown that ERα interacts with both p50 and RELA in vitro and in vivo, and RELA antibody can reduce ERα:ERE complex formation.

RELA can also have a potential role as biomarker for breast, prostate and pancreatic cancers progression and metastases, as suggested by the association found between RELA nuclear localization and prostate cancer aggressiveness and biochemical recurrence. Strong correlation between nuclear localization of RELA and clinicopathological parameters for papillary thyroid carcinoma (PTC), has suggested a role for NF-κB activation in tumor growth and aggressiveness in PTC. Nuclear localization of NF-κB/RELA has been correlated with tumor micrometastases into lymph and blood and negatively correlated with patient survival outcome in patients with head and neck squamous cell carcinoma (HNSCC).

Inventors have discovered modulators of RelA and have shown that blocking RelA/p65 nuclear translocation using these compounds can prevent cancer growth and metastasis. Thus, in embodiments of the various aspects described herein, the compounds of Formula I, II, III, IV or V can inhibit or reduce RelA nuclear localization and thereby prevent transcription activation.

In embodiments of the various aspects disclosed herein, a modulator of RelA function or activity can be a compound of Formula I:

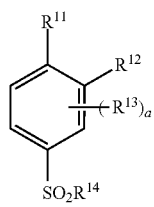

Formula I

In compounds of Formula I, variable a can be 0, 1, 2, or 3. In some embodiments of the various aspects described herein, a is 0.

In compounds of Formula I, $R^{11}$ and $R^{12}$ are independently hydrogen, alkyl, alkenyl, alkynyl, halogen, aryl, heteroaryl, cyclyl, heterocyclyl, carbonyl, carboxy, cyano, hydroxyl, alkoxy, aroxy, nitro, aralkyl, sulfinyl, sulfonyl, thiocabonyl, thio, alkylthio, arylthio, amino, aminoalkyl, mono- or di-alkylamino, arylamino, heteroarylamino or $CF_3$, each of which can be optionally substituted with 1, 2, 3, 4, or 5 substituents. Without limitations, $R^{11}$ and $R^{12}$ can be same or different. In some embodiments, $R^{11}$ and $R^{12}$ are same. In some other embodiments, $R^{11}$ and $R^{12}$ are different.

In various embodiments, $R^{11}$ and $R^{12}$ can be selected independently from hydrogen, halogen, nitro, cyano, $C_1$-$C_6$allkyl, $C_1$-$C_6$alkoxy, acyl, thiol, hydroxyl, carboxylic acid, trifluormethyl, amino, $C_1$-$C_6$alkylamino, di($C_1$-$C_6$alkyl)amino, or —$CO_2$($C_1$-$C_6$alkyl). In some embodiments, $R^{11}$ and $R^{12}$ can be selected independently from halogen, nitro, cyano, trifluoromethyl, carboxylic acid, or amino.

In some embodiments, $R^{11}$ is a halogen. Exemplary halogens for $R^{11}$ are fluoro, bromo or chloro. In one embodiment, $R^{11}$ is fluoro.

In various embodiments, $R^{12}$ can be selected from hydrogen, nitro, cyano, trifluoromethyl, carboxylic acid, amino, $C_1$-$C_6$alkylamino, or $C_1$-$C_6$dialkylamino. In some embodiments, $R^{12}$ is nitro, cyano or trifluromethyl. In one embodiment, $R^{12}$ is nitro.

In some embodiments, $R^{11}$ is halogen and $R^{12}$ is nitro. In one embodiment, $R^{11}$ is fluoro and $R^{12}$ is nitro.

In various embodiments, $R^{13}$ can be selected independently for each occurrence from alkyl, alkenyl, alkynyl, halogen, aryl, heteroaryl, cyclyl, heterocyclyl, carbonyl, carboxy, cyano, hydroxyl, alkoxy, aroxy, nitro, aralkyl, sulfinyl, sulfonyl, thiocabonyl, thio, alkylthio, arylthio, amino, aminoalkyl, mono- or di-alkylamino, arylamino, heteroarylamino or $CF_3$, each of which can be optionally substituted with 1, 2, 3, 4, or 5 substituents. In some embodiments, $R^{13}$ is selected independently for each occurrence from halo, nitro, cyano, trifluoromethyl, amino, $C_1$-$C_6$alkylamino, or di($C_1$-C6alkyl)amino.

The substituent $R^{14}$ can be hydrogen, alkyl, alkenyl, alkynyl, halogen, aryl, heteroaryl, cyclyl, heterocyclyl, carbonyl, carboxy, cyano, hydroxyl, alkoxy, aroxy, nitro, aralkyl, sulfinyl, sulfonyl, thiocabonyl, thio, alkylthio, arylthio, amino, aminoalkyl, mono- or di-alkylamino, arylamino, heteroarylamino or $CF_3$, each of which can be optionally substituted with 1, 2, 3, 4 or 5 substituents. In some embodiments, $R^{14}$ is a $C_1$-$C_6$ alkyl group substituted with 1, 2, 3, 4 or 5 substituents. In some embodiments, $R^{14}$ is a $C_1$-$C_6$ alkyl group substituted with 1 or 2 cyclyl, heterocyclyl, aryl, or heteroaryl groups, each of which can be optionally substituted. In some embodiments, $R^{14}$ is a $C_1$-$C_6$ alkyl group substituted with an optionally substituted heterocylyl. In some embodiments, the optionally substituted heterocylyl is morpholine. In one embodiment, $R^{14}$ is 3-morpholinopropyl.

In some embodiments, a compound of Formula I is CRL1101, having the structure:

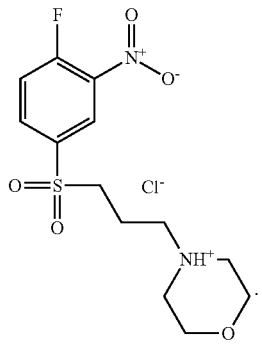 [SMILES: O=[N+]([O-])c1cc(S(=O)(=O)CCC[NH+]2CCOCC2)ccc1F ; [Cl-]]

In various aspects described herein, a modulator of RelA function or activity can be a compound of Formula II:

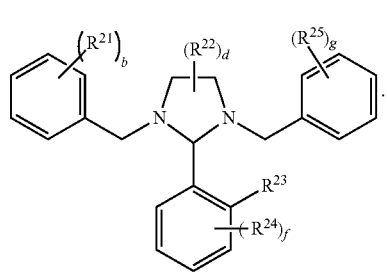

Formula II

In compounds of Formula II, b and g are independently 0, 1, 2, 3, 4 or 5. In various embodiments, b can be 0, 1 or 2. In some embodiments, b is 0. Likewise, g can be 0, 1 or 2 in the various embodiments. In some embodiments, g is 0. Without limitations, b and g can be same or different. In some embodiments, b and g are same. In one embodiment, b and g are both 0.

Variable d in compounds of Formula II can be 0, 1 or 2. In some embodiments, d is 0 or 1. In one embodiment, d is 0.

In compounds of Formula II, f can be 0, 1, 2, 3 or 4. In various embodiments, f can be 0, 1 or 2. In some embodiments, f is 0 or 1. In one embodiment, f is 0.

In some embodiments, b, d, f and g are independently 0 or 1. In one embodiment, b, d, f and g all are 0.

In compounds of Formula II, $R^{21}$, $R^{24}$ and $R^{25}$ are independently for each occurrence hydrogen, alkyl, alkenyl, alkynyl, halogen, aryl, heteroaryl, cyclyl, heterocyclyl, carbonyl, carboxy, cyano, hydroxyl, alkoxy, aroxy, nitro, aralkyl, sulfinyl, sulfonyl, thiocabonyl, thio, alkylthio, arylthio, amino, aminoalkyl, mono- or di-alkylamino, arylamino, heteroarylamino or $CF_3$, each of which can be optionally substituted with 1, 2, 3, 4, or 5 substituents. In some embodiments, $R^{21}$, $R^{24}$ and $R^{25}$ are selected independently, for each occurrence, from halogen, nitro, cyano, $C_1$-$C_6$allkyl, $C_1$-$C_6$alkoxy, acyl, thiol, hydroxyl, carboxylic acid, trifluormethyl, amino, $C_1$-$C_6$alkylamino, di($C_1$-$C_6$alkyl)amino, or —$CO_2$($C_1$-$C_6$alkyl). Without limitations, $R^{21}$, $R^{24}$ and $R^{25}$, when present, can be same, all different, or some same and some different.

In some embodiments, $R^{21}$ and $R^{24}$ are same. In some embodiments, $R^{21}$ and $R^{25}$ are same. In some embodiments, $R^{24}$ and $R^{25}$ are same. In some embodiments, $R^{21}$ and $R^{24}$ are different. In some embodiments, $R^{21}$ and $R^{25}$ are different. In some embodiments, $R^{24}$ and $R^{25}$ are different.

In various embodiments, each $R^{22}$ can be selected independently from alkyl, alkenyl, alkynyl, halogen, aryl, heteroaryl, cyclyl, heterocyclyl, carbonyl, carboxy, cyano, hydroxyl, alkoxy, aroxy, nitro, aralkyl, sulfinyl, sulfonyl, thiocabonyl, thio, alkylthio, arylthio, amino, aminoalkyl, mono- or di-alkylamino, arylamino, heteroarylamino or $CF_3$, each of which can be optionally substituted with 1, 2, 3, 4 or 5 substituents. In some embodiments, when d is 2, the two $R^{22}$ groups with the carbon atoms they are attached to form a 5-8 membered cyclyl, heterocylyl, aryl or heteroaryl, each of which can be optionally substituted with 1, 2, 3 or 4 substituents.

In compounds of Formula II, $R^{23}$ can be selected from hydrogen, alkyl, alkenyl, alkynyl, halogen, aryl, heteroaryl, cyclyl, heterocyclyl, carbonyl, carboxy, cyano, hydroxyl, alkoxy, aroxy, nitro, aralkyl, sulfinyl, sulfonyl, thiocabonyl, thio, alkylthio, arylthio, amino, aminoalkyl, mono- or di-alkylamino, arylamino, heteroarylamino or $CF_3$, each of which can be optionally substituted with 1, 2, 3, 4, or 5 substituents. In some embodiments, $R^{23}$ can be selected from hydrogen, halogen, nitro, cyano, $C_1$-$C_6$allkyl, $C_1$-$C_6$alkoxy, acyl, thiol, hydroxyl, carboxylic acid, trifluormethyl, amino, $C_1$-$C_6$alkylamino, di($C_1$-$C_6$alkyl)amino, or —$CO_2$($C_1$-$C_6$alkyl). In some embodiments, $R^{23}$ is hydrogen, hydroxyl or $C_1$-$C_3$alkoxy. In one embodiment, $R^{23}$ is hydroxyl.

In some embodiments of the various aspects described herein, a compound of Formula II is CRL1102 having the structure:

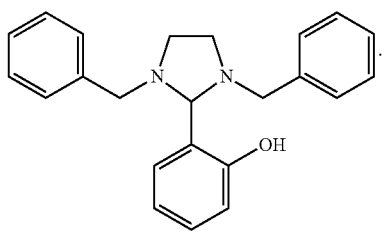 [SMILES: Oc1ccccc1C1N(Cc2ccccc2)CCN1Cc1ccccc1]

In various aspects described herein, a modulator of RelA can be a compound of Formula III:

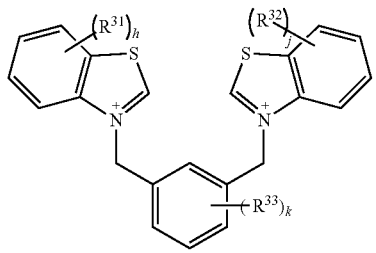

Formula III

In compounds of Formula III, h, j and k are independently 0, 1, 2, 3 or 4. Without limitations, h, j and k can all be same, all different or two are same and the third is different. In some embodiments, h is 0 or 1. In one embodiment, h is 0. In some embodiments, j is 0 or 1. In one embodiment, j is 0. In some embodiments, k is 0 or 1. In one embodiment, k is 0.

In some embodiments, h and j are independently 0, 1 or 2. In some embodiments, h and k are independently 0, 1 or 2. In some embodiments, j and k are independently 0, 1 or 2. In some embodiments, h, j and k are independently 0 or 1. In one embodiment, h, j and k all are 0.

In various embodiments, $R^{31}$, $R^{32}$ and $R^{33}$ can be selected independently for each occurrence from and are independently for each occurrence alkyl, alkenyl, alkynyl, halogen, aryl, heteroaryl, cyclyl, heterocyclyl, carbonyl, carboxy, cyano, hydroxyl, alkoxy, aroxy, nitro, aralkyl, sulfinyl, sulfonyl, thiocabonyl, thio, alkylthio, arylthio, amino, aminoalkyl, mono- or di-alkylamino, arylamino, heteroarylamino or $CF_3$, each of which can be optionally substituted with 1, 2, 3, 4, or 5 substituents. Without limitations, $R^{31}$, $R^{32}$ and $R^{33}$ can all be same, all different or two are same and the third is different. In some embodiments, $R^{31}$ and $R^{32}$ are same. In some embodiments, $R^{31}$ and $R^{33}$ are same. In some embodiments, $R^{32}$ and $R^{33}$ are same.

In some embodiments, $R^{31}$ and $R^{32}$ are different. In some embodiments, $R^{31}$ and $R^{33}$ are different. In some embodiments, $R^{32}$ and $R^{33}$ are different.

In some embodiments, $R^{31}$, $R^{32}$ and $R^{33}$ can be selected independently for each occurrence from halogen, nitro, cyano, $C_1$-$C_6$allkyl, $C_1$-$C_6$alkoxy, acyl, thiol, hydroxyl, carboxylic acid, trifluormethyl, amino, $C_1$-$C_6$alkylamino, di($C_1$-$C_6$alkyl)amino, or —$CO_2$($C_1$-$C_6$alkyl). In some embodiments, $R^{31}$, $R^{32}$ and $R^{33}$ can be selected independently for each occurrence from hydrogen, hydroxyl or $C_1$-$C_3$alkoxy.

In various embodiments, $R^{34}$ can be selected independently for each occurrence from alkyl, alkenyl, alkynyl, cyclyl, heterocylyl, aryl or heteroaryl, each of which can be optionally substituted with 1, 2, 3, 4 or 5 substituents.

In some embodiments of the various aspects described herein, a compound of Formula III is CRL11021 having the structure:

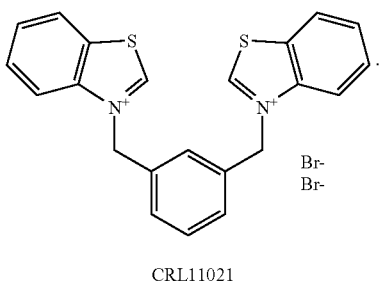 [SMILES: c1cc(C[n+]2csc3ccccc32)cc(C[n+]2csc3ccccc32)c1]

CRL11021

In various aspects described herein, a modulator of RelA can be a compound of Formula IV:

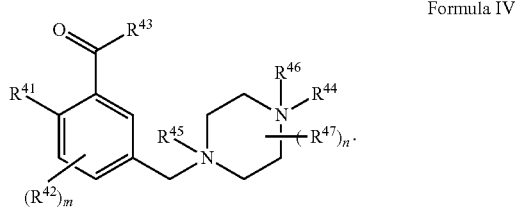

Formula IV

In compounds of Formula IV, m is 0, 1, 2 or 3. In some embodiments, m is 0 or 1. In one embodiment, m is 0.

In various embodiments, n can be selected from 0, 1, 2, 3 or 4. In some embodiments, n is 0 or 1. In one embodiment, n is 0.

In compounds of Formula IV, $R^{41}$ can be selected from hydrogen, alkyl, alkenyl, alkynyl, halogen, aryl, heteroaryl, cyclyl, heterocyclyl, carbonyl, carboxy, cyano, hydroxyl, alkoxy, aroxy, nitro, aralkyl, sulfinyl, sulfonyl, thiocabonyl, thio, alkylthio, arylthio, amino, aminoalkyl, mono- or di-alkylamino, arylamino, heteroarylamino or $CF_3$, each of which can be optionally substituted with 1, 2, 3, 4, or 5 substituents. In some embodiments, $R^{41}$ can be selected from hydrogen, halogen, nitro, cyano, $C_1$-$C_6$allkyl, $C_1$-$C_6$alkoxy, acyl, thiol, hydroxyl, carboxylic acid, trifluormethyl, amino, $C_1$-$C_6$alkylamino, di($C_1$-$C_6$alkyl)amino, or —$CO_2$($C_1$-$C_6$alkyl). In some embodiments, $R^{41}$ is hydrogen, hydroxyl or $C_1$-$C_3$alkoxy. In one embodiment, $R^{41}$ is hydroxyl.

In various embodiments, $R^{42}$ can be selected independently for each occurrence from alkyl, alkenyl, alkynyl, halogen, aryl, heteroaryl, cyclyl, heterocyclyl, carbonyl, carboxy, cyano, hydroxyl, alkoxy, aroxy, nitro, aralkyl, sulfinyl, sulfonyl, thiocabonyl, thio, alkylthio, arylthio, amino, aminoalkyl, mono- or di-alkylamino, arylamino, heteroarylamino or $CF_3$, each of which can be optionally substituted with 1, 2, 3, 4, or 5 substituents. In some embodiments, $R^{42}$ is selected independently for each occurrence from halo, nitro, cyano, trifluoromethyl, amino, $C_1$-$C_6$alkylamino, or di($C_1$-$C6$alkyl)amino.

In embodiments of the various aspects described herein, $R^{43}$ can be hydrogen, alkyl, alkenyl, alkynyl, aryl, heteroaryl, cyclyl, heterocyclyl, hydroxyl, alkoxy, aroxy, nitro, aralkyl, sulfinyl, sulfonyl, thiocabonyl, thio, alkylthio, arylthio, amino, aminoalkyl, mono- or di-alkylamino, arylamino, heteroarylamino or $CF_3$, each of which can be optionally substituted with 1, 2, 3, 4 or 5 substituents. In some embodiments, $R^{43}$ is hydrogen or $C_1$-$C_6$ alkyl, which can be optionally substituted. In one embodiment, $R^{43}$ is methyl, ethyl propyl, butyl or t-butyl. In one embodiment, $R^{43}$ is methyl.

In compounds of Formula IV, $R^{44}$ can be selected from hydrogen, alkyl, alkenyl, alkynyl, aryl, heteroaryl, cyclyl, heterocyclyl, aralkyl, sulfinyl, sulfonyl, carbonyl, carboxy, thiocabonyl, thio, alkylthio, arylthio or $CF_3$, each of which can be optionally substituted with 1, 2, 3, 4 or 5 substituents. In some embodiments, $R^{44}$ is hydrogen or $C_1$-$C_6$ alkyl, which can be optionally substituted. In one embodiment, $R^{44}$ is methyl, ethyl propyl or butyl. In one embodiment, $R^{44}$ is methyl.

In compounds of Formula IV, $R^{45}$ and $R^{46}$ are independently for each occurrence absent, hydrogen, alkyl, alkenyl, alkynyl, aryl, heteroaryl, cyclyl, heterocyclyl, aralkyl, sulfinyl, sulfonyl, carbonyl, carboxy, thiocabonyl, thio, alkylthio, arylthio or $CF_3$ with 1, 2, 3, 4 or 5 substituents. It is noted that when either of $R^{45}$ or $R^{46}$ is present, the nitrogen to which it is attached has a positive charge. Further, $R^{45}$ and $R^{46}$ can be same or different. In some embodiments, $R^{45}$ and $R^{46}$ are independently absent, hydrogen or $C_1$-$C_6$ alkyl, which can be optionally substituted. In one embodiment, $R^{45}$ is hydrogen. In one embodiment, $R^{46}$ is hydrogen. In one embodiment, $R^{45}$ and $R^{46}$ both are hydrogen.

In various embodiments, $R^{47}$ can be selected independently for each occurrence from alkyl, alkenyl, alkynyl, halogen, aryl, heteroaryl, cyclyl, heterocyclyl, carbonyl, carboxy, cyano, hydroxyl, alkoxy, aroxy, nitro, aralkyl, sulfinyl, sulfonyl, thiocabonyl, thio, alkylthio, arylthio, amino, aminoalkyl, mono- or di-alkylamino, arylamino, heteroarylamino or $CF_3$, each of which can be optionally substituted with 1, 2, 3, 4 or 5 substituents.

In some embodiments of the various aspects described herein, a compound of Formula IV is CRL1103 having the structure:

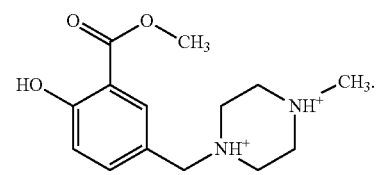 [SMILES: COC(=O)c1cc(C[NH+]2CC[NH+](C)CC2)ccc1O]

In various aspects described herein, a modulator of RelA can be a compound of Formula V:

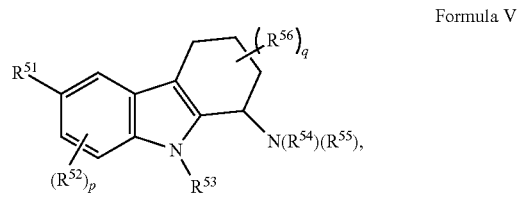

Formula V

In compounds of Formula V, p and q are independently 0, 1, 2 or 3. In various embodiments, p and q can be same or they can be different. In some embodiments, p is 0 or 1. In one embodiment, p is 0. In some embodiments, q is 0 or 1. In one embodiment, q is 0. In some embodiments, p and q are independently 0 or 1. In one embodiment, p and q both are 0.

In various embodiments, $R^{51}$ can be selected from hydrogen, alkyl, alkenyl, alkynyl, halogen, aryl, heteroaryl, cyclyl, heterocyclyl, carboxy, cyano, hydroxyl, alkoxy, aroxy, nitro, aralkyl, sulfinyl, sulfonyl, thiocabonyl, thio, alkylthio, arylthio, amino, aminoalkyl, mono- or di-alkylamino, arylamino, heteroarylamino or $CF_3$, each of which can be optionally substituted with 1, 2, 3, 4, or 5 substituents. In some embodiments, $R^{51}$ can be selected from hydrogen, cyclyl, heteroycly, aryl, heteroaryl, halogen, nitro, cyano, $C_1$-$C_6$allkyl, $C_1$-$C_6$alkoxy, acyl, thiol, hydroxyl, carboxylic acid, trifluormethyl, amino, $C_1$-$C_6$alkylamino, di($C_1$-$C_6$alkyl)amino, or —$CO_2$($C_1$-$C_6$alkyl). In some embodiments, $R^{51}$ is an optionally substituted aryl or heteroaryl. In some embodiments, $R^{51}$ is optionally substituted phenyl.

In compounds of Formula V, $R^{52}$ and $R^{56}$ can be selected independently for each occurrence from alkyl, alkenyl, alkynyl, halogen, aryl, heteroaryl, cyclyl, heterocyclyl, carbonyl, carboxy, cyano, hydroxyl, alkoxy, aroxy, nitro, aralkyl, sulfinyl, sulfonyl, thiocabonyl, thio, alkylthio, arylthio, amino, aminoalkyl, mono- or di-alkylamino, arylamino, heteroarylamino or $CF_3$, each of which can be optionally substituted with 1, 2, 3, 4, or 5 substituents. Without limitations, $R^{52}$ and $R^{56}$ can be the same or different.

Without limitations, $R^{53}$ can be hydrogen, alkyl, alkenyl, alkynyl, aryl, heteroaryl, cyclyl, heterocyclyl, aralkyl, sulfinyl, sulfonyl, carbonyl, carboxy, thiocabonyl, thio, alkylthio, arylthio or $CF_3$, each of which can be optionally substituted with 1, 2, 3, 4 or 5 substituents. In some embodiments, $R^{53}$ can be selected from hydrogen or $C_1$-$C_6$alkyl, which can be optionally substituted. In one embodiment, $R^{53}$ is hydrogen.

In compounds of Formula V, $R^{54}$ and $R^{55}$ can be independently hydrogen, alkyl, alkenyl, alkynyl, aryl, heteroaryl, cyclyl, heterocyclyl, aralkyl, sulfinyl, sulfonyl, carbonyl, carboxy, thiocabonyl, thio, alkylthio, arylthio or $CF_3$, each of which can be optionally substituted with 1, 2, 3, 4 or 5 substituents. Without limitations $R^{54}$ and $R^{55}$ can be same or different. In some embodiments, at least one of $R^{54}$ and $R^{55}$ is hydrogen. In some embodiments, both of $R^{54}$ and $R^{55}$ are hydrogen. In some embodiments, at least one of $R^{54}$ and $R^{55}$ is not hydrogen. In some embodiments, both of $R^{54}$ and $R^{55}$ are not hydrogen. In some embodiments, one of $R^{54}$ and $R^{55}$ is hydrogen and the other is not hydrogen.

In various embodiments, $R^{54}$ can be selected from hydrogen, $C_1$-$C_6$alkyl, cyclyl, heterocyclyl, aryl or heteroaryl, each of which can be optionally substituted. In some embodiments, $R^{54}$ is hydrogen or $C_1$-$C_6$alkyl optionally substituted with 1 or 2 substituents. In some embodiments, $R^{54}$ is a $C_1$-$C_6$alkyl substituted with a hydroxyl, aryl, heteroaryl, alkoxy, or halogen. In some embodiments, $R^{54}$ is benzyl or 2-hydroxyethyl.

In various embodiments, $R^{55}$ can be selected from hydrogen, $C_1$-$C_6$alkyl, cyclyl, heterocyclyl, aryl or heteroaryl, each of which can be optionally substituted. In some embodiments, $R^{55}$ is hydrogen or $C_1$-$C_6$alkyl optionally substituted with 1 or 2 substituents. In some embodiments, $R^{55}$ is a $C_1$-$C_6$alkyl substituted with a hydroxyl, aryl, heteroaryl, alkoxy, or halogen. In some embodiments, $R^{55}$ is benzyl or 2-hydroxyethyl.

In some embodiments of the various aspects described herein, a compound of Formula V is CRL1104 having the structure:

In some embodiments of the various aspects described herein, a compound of Formula V is CRL11041 having the structure:

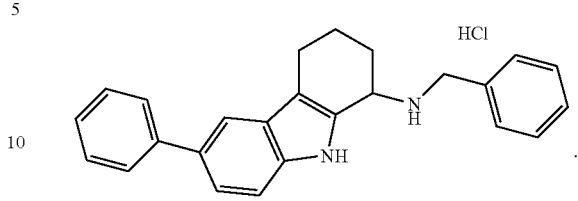

It is noted that stereoisomers, pharmaceutically acceptable salts, and prodrugs of compounds of Formula I, II, III, IV and V are also provided herein.

In some embodiments, the compounds of Formula I, II, III, IV and V are reversible inhibitors of RelA/p65 function or activity. This is in contrast to the irreversible inhibitors known in the art. The term "reversible inhibitor" is used herein to refer to a compound that associates with RelA/p65 in such a way as to inhibit the activity of the RelA/p65 while the RelA/p65 and inhibitor are bound, but does not associate with RelA/p65 in such a way as to inhibit the activity of the RelA/p65 when the RelA/p65 and inhibitor are no longer bound.

The compounds of described herein can be synthesized using methods known in the art and available to one of ordinary skill in the art. Some exemplary compounds of Formulas (I0-(IV) are also available from commercial vendors, such as, ChemBridge Corporation, San Diego, Calif.

In embodiments of the various aspects described herein, the compounds of Formula I, II, III, IV or V can be formulated as particles, e.g. nano- or microparticles. Formulation of the compound into particles can be advantageous. As used herein, the term "nanoparticle" refers to particles that are on the order of $10^{-9}$ or one billionth of a meter and below $10^{-6}$ or 1 millionth of a meter in size. The term "nanoparticle" includes nanospheres; nanorods; nanoshells; and nanoprisms; and these nanoparticles may be part of a nanonetwork. The term "nanoparticles" also encompasses liposomes and lipid particles having the size of a nanoparticle. The particles may be, e.g., monodisperse or polydisperse and the variation in diameter of the particles of a given dispersion may vary, e.g., particle diameter of between about 0.1 to 100's of nm. Without limitations, the compounds of Formula I, II, III, IV or V can be formulated in any type of nanparticle, including, but not limited to, liposomes, emulsions, microemulsions, nanoemulsions, self-microemulsifying drug delivery systems (SMEDDS), polymeric nanoparticles, solid-lipid nanoparticles, nanostructured liquid crystals, and the like.

Generally there are at least seven types of nanoparticles that can be formulated: (1) nanoparticles formed from a polymer or other material to which a compound of Formula I, II, III, IV or V absorbs/adsorbs or forms a coating on a nanoparticle core; (2)) nanoparticles formed from a core formed by the compound of Formula I, II, III, IV or V, which is coated with a polymer or other material; (3) nanoparticles formed from a polymer or other material to which a compound of Formula I, II, III, IV or V is covalently linked; (4) nanoparticles formed from compound of Formula I, II, III, IV or V and other molecules; (5) nanoparticles formed so as to comprise a generally homogeneous mixture of a compound of Formula I, II, III, IV or V with a constituent of the nanoparticle or other non-drug substance; (6) nanoparticles of a pure drug or drug mixtures with a coating over a core of a compound of Formula I, II, III, IV or V; and (7) nanoparticles composed entirely of a compound of Formula I, II, III, IV or V.

In some embodiments, the nanoparticle is of size about 1 nm to about 1000 nm, about 50 nm to about 500 nm, about 100 nm to about 250 nm, or about 200 nm to about 350 nm. In one embodiment, the nanoparticle is of about 100 nm to about 1000 nm. In another embodiment, the nanoparticle is of size about 80 nm to about 200 nm. In one embodiment, nanoparticle is of size about 50 nm to about 500 nm. In some embodiments, nanparticle is of size about 158 nm, about 218 nm, or about 305 nm. In some embodiments, nanoparticle is of size about 337 nm, about 526 nm, about 569 nm, about 362 nm, about 476 nm, about 480 nm, about 676 nm, about 445 nm, about 434 nm, about 462 nm, about 492 nm, about 788 nm, about 463 nm, or about 65 nm Nanoparticles described herein usually have a narrow size distribution as measured by Polydispersity Index (PdI). As used herein, the term "polydispersity index" is a measure of the distribution broadness of a sample, and is typically defined as the relative variance in the correlation decay rate distribution, as is known by one skilled in the art. See B J. Fisken, "Revisiting the method of cumulants for the analysis of dynamic light-scattering data," Applied Optics, 40(24), 4087-4091 (2001) for a discussion of cumulant diameter and polydispersity. Generally, the polydispersity of the nanoparticles described herein is less than about 0.8. In some embodiments, the polydispersity of the nanoparticles is less than about 0.5, less than about 0.4, less than about 0.3, less than about 0.25, less than about 0.2, less than about 0.15, less than about 0.1, or less than about 0.05. In some embodiments, the polydispersity of the nanoparticles is about 0.072, about 0.1, about 0.149, or about 0.236, about 0.165, about 0.221, about 0.177, about 0.213, about 0.264, about 0.241, about 0.251, about 0.273, about 0.211, about 0.181, about 0.249, about 0.298, about 0.348, or about 0.282.

Without limitations, the nanoparticle can comprise other components in addition to the compound of Formula I, II, III, IV or V. For example, the nanoparticle can comprise one or more of polymers, anionic polymers, cationic polymers, amphiphilic polymers, surfactants, lipids, phospholipids, cationic lipids, amphiphilic lipids, excipients and the like. If present in nanoparticle, each of the additional component can be present in an amount ranging from about 0.01% to about 90%, e.g., from about 0.01% to about 80%, from about 0.01% to about 70%, from about 0.01% to about 60%, from about 0.01% to about 50%, from about 0.01% to about 40%, from about 0.01% to about 30%, from about 0.01% to about 25%, of the total weight of the nanoparticle. It is to be understood that amount of a component is independent from the amount of a second component in the liposome or the emulsion.

A surfactant that can be added to the nanoparticle can be any of anionic, cationic, ampholytic and nonionic surfactants. Examples anionic surfactants include fatty esters such as sodium stearate, potassium oleate and semicurable tallow fatty acid sodium; alkyl sulfates such as sodium dodecyl sulfate, tri(2-hydroxyethyl) ammonium dodecyl sulfate and sodium octadecyl sulfate; benzensulfonates such as sodium nonyl benzanesulfonate, sodium dodecyl benzenesulfonate, sodium otadecyl benzenesulfonate and sodium dodecyl diphenylether disulfonate; naphthalenesulfonates such as sodium dodecyl naphthalenesulfonate and naphthalene-sulfonic acid formalin condensates; sulfosuccinates such as sodium didodecyl sulfosuccinate and sodium dioctadecyl sulfosuccinate; polyoxyethylene sulfates such as sodium polyoxyethylenedodecylether sulfate, tri(2-hydroxyethyl) ammonia polyoxyethylene dodecylether sulfate, sodium polyoxyethylene octadecylether sulfate and sodium polyoxyethylene dodecylphenylether sulfate; and phosphates such as potassium dodecyl phosphate and sodium octadecyl phosphate. Examples of cationic surfactants include alkyl amine salts such as octadecyl ammonium acetate and coconut oil amine acetate; and fourth ammonia salts such as dodecyl trimethyl ammonium chloride, octadecyl trimethyl ammonium chloride, dioctadecyl dimethyl ammonium chloride and dodecyl benzyl dimethyl ammonium chloride. Examples of ampholytic surfactants include alkyl betains such as dodecyl betain and octadodecyl betain; and amine oxides such as dodecyl dimethyl amine oxide. Examples of nonionic surfactants include polyoxyethylene alkyl ethers such as polyoxyethylene dodecyl ether, polyoxyethylene hexadecyl ether, polyoxyethylene octadecyl ether and polyoxyethylene (9-octadecenyl) ether; polyoxyethylene phenyl ethers such as polyoxyethylene octylphenyl ether and polyoxyethylene nonylphenyl ether; oxirane polymers such as polyethylene oxide and copolymer of ethylene oxide and propylene oxide; sorbitan fatty esters such as sorbitan dodecanoic ester, sorbitan hexadecanoic ester, sorbitan octadecanoic ester, sorbitan (9-octadecenoic) ester, sorbitan (9-octadecenoic) triester, polyoxyethylene sorbitan dodekanoic ester, polyoxyethylene sorbitan hexadecanoic ester, polyoxyethylene sorbitan octadecanoic ester, polyoxyethylene sorbitan octanoic triester, polyoxyethylene sorbitan (9-octadecenoic) ester and polyoxyethylene sorbitan (9-octadecenoic) triester; sorbitol fatty esters such as polyoxyethylene sorbitol (9-octadecenoic) tetraester; glycerin fatty esters such as glycerin octadecanoic ester and glycerin (9-octadecenoic) ester; polyalkylene oxide block copolymers such poloxomers (commercially available under the trademark PLURONIC® (BASF)).

Suitable commercially available amphoteric surfactants include, but are not limited to, MIRANOL® HMA sodium lauroampho acetate (38% solids) and MIRANOL® ULTRA L32 sodium lauroampho acetate available from Rhodia Novecare (Cranbury, N.J.). Suitable commercially available linear alcohol ethoxylates include, but are not limited to, SURFONIC® L12-6 six-mole ethoxylate of linear, primary 10-12 carbon number alcohol available from Huntsman Performance Products (The Woodlands, Tex.). Suitable commercially available alkyl sulfates include, but are not limited to, POLYSTEP® B-29 sodium octyl sulfate available from Stepan Company (Northfield, 111.). Suitable commercially available nonionic surfactants include, but are not limited to, oxo-alcohol polyglycol ethers such as GENAPOL® UD 070 CI 1-oxo-alcohol polyglycol ether (7 EO) available from Clamant Corporation (Cranbury, N.J.). Suitable commercially available linear alkylbenzene sulfonic acids and their salts include, but are not limited to, NAXSOFT® 98S dodecyl Benzene Sulfonic Acid and NAXSOFT® 40S Sodium dodecyl Benzene sulfonate available from Nease Corporate (Cincinnati, Ohio).

In some embodiments, the compound of Formula I, II, III, IV or V can be formulated in liposomes. As used herein, the term "liposome" encompasses any compartment enclosed by a lipid layer, which can be a monolayer or a bilayer. Liposomes may be characterized by membrane type and by size. Liposomes are also referred to as lipid vesicles in the art. In order to form a liposome the lipid molecules comprise elongated non-polar (hydrophobic) portions and polar (hydrophilic) portions. The hydrophobic and hydrophilic portions of the molecule are preferably positioned at two ends of an elongated molecular structure. When such lipids are dispersed in water they spontaneously form bilayer membranes referred to as lamellae or self arranged vesicles. The lamellae are composed of two mono layer sheets of lipid molecules with their non-polar (hydrophobic) surfaces facing each other and their polar (hydrophilic) surfaces facing the aqueous medium. The membranes formed by the lipids enclose a portion of the aqueous phase in a manner similar to that of a cell membrane enclosing the contents of a cell. Thus, the bilayer of a liposome has similarities to a cell membrane without the protein components present in a cell membrane.

The liposomes that are used in the present invention are preferably formed from lipids which when combined form relatively stable vesicles. An enormous variety of lipids are known in the art which can be used to generate such liposomes. Preferred lipids include, but are not limited to, neutral and negatively charged phospholipids or sphingolipids and sterols, such as cholesterol. The selection of lipids is generally guided by consideration of, e.g., liposome size and stability in the personal care composition.

Liposomes include unilamellar vesicles which are comprised of a single lipid layer and generally have a diameter of 20 to 100 nanometers; large unilamellar vesicles (LUVS) are typically larger than 100 nm, which can also be produced by subjecting multilamellar liposomes to ultrasound. In some embodiments, liposomes have a diameter in the range of 20 nm to 400 nm.

Liposomes can further comprise one or more additional lipids and/or other components such as sterols, e.g., cholesterol. Additional lipids can be included in the liposome compositions for a variety of purposes, such as to prevent lipid oxidation, to stabilize the bilayer, to reduce aggregation during formation or to attach carriers onto the liposome surface. Any of a number of additional lipids and/or other components can be present, including amphipathic, neutral, cationic, anionic lipids, and programmable fusion lipids. Such lipids and/or components can be used alone or in combination.

Liposome compositions can be prepared by a variety of methods that are known in the art. See e.g., U.S. Pat. Nos. 4,235,871; 4,737,323; 4,897,355 and 5,171,678; published International Applications WO1996/14057 and WO1996/37194; Felgner, P. L. et al., *Proc. Natl. Acad. Sci*., USA (1987) 8:7413-7417, Bangham, et al. *M. Mol. Biol*. (1965) 23:238, Olson, et al. *Biochim. Biophys. Acta* (1979) 557:9, Szoka, et al. *Proc. Natl. Acad. Sci*. (1978) 75: 4194, Mayhew, et al. *Biochim. Biophys. Acta* (1984) 775:169, Kim, et al. *Biochim. Biophys. Acta* (1983) 728:339, and Fukunaga, et al. *Endocrinol*. (1984) 115:757, content of all of which is incorporated herein by reference.

In some embodiments, the compound of Formula I, II, III, IV or V can be formulated in an emulsion. As used herein, "emulsion" is a heterogenous system of one liquid dispersed in another in the form of droplets. Emulsions are often biphasic systems comprising two immiscible liquid phases intimately mixed and dispersed with each other. Either of the phases of the emulsion can be a semisolid or a solid, as is the case of emulsion-style ointment bases and creams. The compound can be present as a solution in the aqueous phase, oily phase or itself as a separate phase.

In some embodiments, the compositions are formulated as nanoemulsions. The term "nanoemulsion" means an emulsion wherein the particles are of sized in the nanometer scale. Nanoemuslions also include thermodynamically stable, isotropically clear dispersions of two immiscible liquids that are stabilized by interfacial films of surface-active molecules. The application of emulsion formulations via dermatological, oral and parenteral routes and methods for their manufacture have been reviewed in the literature, for example see Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., volume 1, p. 245; and Block, in Pharmaceutical Dosage Forms, Lieberman, Rieger and Banker (Eds.), 1988, Marcel Dekker, Inc., New York, N.Y., volume 1, p. 335, content of all of which is herein incorporated by reference in its entirety.

In some embodiments, the compound can be formulated in a polymeric nanoparticle. As used herein, the term "polymeric nanoparticle" refers to a carrier system in which the compound of Formula I, II, III, IV or V is retained, encapsulated or adsorbed. The term polymeric nanoparticles can be used to denote nanospheres and nanocapsules. Nanospheres are constituted of a polymer matrix in which the compound is retained, encapsulated or adsorbed. Nanocapsules are constituted of a polymer container enclosing a nucleus, in which the compound can be dissolved, retained, or dispersed in the nucleus and/or adsorbed in the polymeric wall.

Overall, the production processes for polymer nanoparticles can be classified among the methods of in situ polymerisation or methods using pre-formed polymers. Polymers commonly used in the preparation of nanoparticles are, for example poly (lactide), poly (lactideglycolide), poly (glycolide), poly (caprolactone), poly (amides), poly (anhydrides), poly (amino acids), poly (esters), poly (cyanoacrylates), poly (phosphazines), poly (phosphoesters), poly (esteramides), poly (dioxanones), poly (acetals), poly (cetals), poly (carbonates), poly (orthocarbonates), degradable poly (urethanes), chitins, chitosans, poly (hydroxybutyrates), poly (hydroxyvalerates), poly (maleic acid), poly (alkylene oxalates), poly (alkylene succinates), poly (hydroxybutyrates-co-hydroxyvalerates), and copolymers, terpolymers, oxidised cellulose, or combinations or mixtures of these materials. Some polymers that prove to be especially interesting are poly (e-caprolactone) (PCL; for example, poly (E-caprolactone) 65 Kd—Sigma Aldrich); methacryllate acid copolymers and methacryllate or acrylic esters (e.g. EUDRAGITS®); poly (alkyl methacrylate); poly (methyl methacryllate) (e.g. PMM).

Polymeric nanoparticles can be produced, for example, by the methods (i) of in situ polymerisation of monomers (latex) or dispersion of pre-formed polymers (pseudolatex or artificial latex) as described in De Jaeghere F et al. Nanoparticles. In: Mathiowitz E, ed. *The Encyclopedia of Controlled Drug Delivery*. New York, N.Y.: Wiley and Sons Inc; 1999: 641-664 and Couvreur P, et al. Controlled drug delivery with nanoparticles: *Eur J Pharm Biopharm*. 1995; 41: 2-13; (ii) method of emulsion-evaporation for pharmaceutical use first proposed by Gurny R, Peppas N A, Harrington D D, Banker G S. Development of biodegradable and injectable lattices for controlled release of potent drugs. *Drug Dev Ind Pharm*. 1981; 7: 1-25 based on U.S. Pat. No. 4,177,177, with the polymer being dissolved in a volatile organic solvent immiscible in water. The organic solution is dispersed in an aqueous phase containing emulsifier and oil/water emulsion forming facilitators; and (iii) method of the interface deposit of pre-formed polymers (nanoprecipitation) as described by Fessi et al. in U.S. Pat. No. 5,049,322. Content of all references cites in this paragraph is incorporated herein by reference.

The organic solvents that can be used for the preparation of nanoparticles are: small chain alcohols (methanol, ethanol, isopropanol, etc.), small chain ketones (acetone, methyl-ethyl-ketone, etc.), light hydrocarbons or a mixture of light hydrocarbons (hexane, petroleum ether, etc.), lightly chlorated hydrocarbons (chloroform, methylene hydrochloride, trihydrochlorideethylene, etc.), or other common light solvents such as acetonitryl, dioxane, etc. Acetone is a particularly interesting solvent.

Surfactants are commonly used to avoid the aggregation of the particles when stored. Examples of surfactants that can be used are: lecithins, synthetic, anionic (e.g. sodium lauryl sulphate), cationic (e.g. quaternary ammonium) or non-ionic (e.g. sorbitan monoesters, containing or not polyoxyethylene residues, ethers formed from fatty alcohols and polyethylene glycol, polyoxyethylene-polypropylene glycol, etc.). Particularly interesting combinations include lipophilic surfactants with low hydrophilic-lipophilic (EHL) balance values (e.g. sorbitan esters—Span 20 or Span 60) and hydrophilic surfactants with high EHL values (ethoxylated sorbitan esters-Tween 80) or, indeed, merely a single non-ionic surfactant having a high EHL (such as Tween 80).

In some embodiments, the compound of Formula I, II, III, IV or V can be formulated in a self-microemulsifying drug delivery system (SMEDDS). A self-microemulsifying drug delivery system can be described as an optically isotropic system of oil, surfactant and drug, which forms an oil in water microemulsion on gentle agitation in the presence of water. A SMEDDS for pharmaceutical application can thus be considered as a concentrate which is rapidly dispersed when introduced to the body to form an oil-in-water microemulsion.

In some embodiments, the compound of Formula I, II, III, IV or V can be formulated in a solid lipid nanoparticle. Solid lipid nanoparticles can be prepared in any manner conventional in the art, such as, for example, as described in Stuchlik, M. and Zak, S. (Lipid-Based Vehicle for Oral Delivery, *Biomed. Papers* 145 (2): 17-26, (2001)). The solid lipid nanoparticle can be prepared in a hot homogenization process by homogenization of melted lipids at elevated temperature. In this process, the solid lipid is melted and the compound of Formula I, II, III, IV or V is dissolved in the melted lipid. A pre-heated dispersion medium is then mixed with the compound-loaded lipid melt, and the combination is mixed with a homogenisator to form a coarse pre-emulsion. High pressure homogenization is then performed at a temperature above the lipids melting point to produce an oil/water-nanoemulsion. The nanoemulsion is cooled down to room temperature to form solid lipid nanoparticles.

Alternatively, the solid lipid nanoparticles can be prepared in a cold homogenization process. In this process, the lipid is melted and the compound of Formula I, II, III, IV or V is dissolved in the melted lipid. The compound-loaded lipid is then solidified in liquid nitrogen or dry ice. The solid compound-lipid is ground in a powder mill to form 50-100 µm particles. The lipid particles are then dispersed in cold aqueous dispersion medium and homogenized at room temperature or below to form solid lipid nanoparticles.

Described herein are small molecule RelA modulators of Formula I, II, III, IV and V for use in methods of treating a subject having or at risk for developing a proliferative disorder, such as a cancer. The compounds of Formula I, II, III, IV and can be administered to a subject in need thereof by any appropriate route which results in an effective treatment in the subject.

Accordingly, in some aspects, provided herein are methods of modulating, e.g., inhibiting RelA/p65 activity or function in a subject. Such methods comprise administering to a subject in need thereof a therapeutically effective amount of a compound of Formula I, II, III, IV or V.

In some aspects, provided herein are methods of treatment of a subject having a cancer or a cancerous condition, or at risk for cancer or a cancerous condition, the methods comprising administering to a subject having a cancer or cancerous condition, or at risk for cancer or a cancerous condition, a therapeutically effective amount of a compound of Formula I, II, III, IV or V.

In some embodiments of the aspects described herein, the methods of treating, inhibiting, reducing severity of, slowing progression of and/or preventing metastasis of cancer or a cancerous condition further comprise the step of selecting, diagnosing, or identifying a subject having cancer or a cancerous condition. In such embodiments, a subject is identified as having cancer by objective determination of the presence of cancer cells or a tumor in the subject's body by one of skill in the art. Such objective determinations can be performed through the sole or combined use of tissue biopsies, blood and platelet cell counts, urine analyses, magnetic resonance imaging (MRI) scans, computed tomography (CT) scans, liver function studies, chest X-rays and bone scans in addition to the monitoring of specific symptoms associated with a cancer.

The compounds of Formula I, II, III, IV or V can be formulated, dosed, and administered in a fashion consistent with good medical practice for use in the treatment of the cancers and cancerous conditions described herein, such as breast cancer. Factors for consideration in this context include the particular disorder or type of disorder, e.g., cancer, being treated, the particular subject being treated, the clinical condition of the individual subject, the cause of the disorder, the site of delivery of the agent, the method of administration, the scheduling of administration, and other factors known to medical practitioners.

Accordingly, the "therapeutically effective amount" of a compound of Formula I, II, III, IV or V to be administered is governed by such considerations, and, as used herein, refers to the minimum amount necessary to prevent, ameliorate, or treat, or stabilize, a disorder or condition, such as one mediated by binding and/or function of RelA In those aspects and embodiments relating to cancer or other proliferative disorders, the therapeutically effective amount of a compound of Formula I, II, III, IV or V described herein is the minimum amount necessary to, for example, increase the time until progression (duration of progression free survival), to inhibit or prevent tumor invasion, or to treat or prevent the occurrence or recurrence of a tumor, a dormant tumor, or a micrometastases. In some such embodiments, a compound of Formula I, II, III, IV or V is optionally formulated with one or more agents currently used to prevent or treat cancer or a risk of developing a cancer. The effective amount of such other agents depends on the amount of the compound of Formula I, II, III, IV or V present in the formulation, the type of disorder or treatment, and other factors discussed herein, and as understood by one of skill in the art. These are generally used in the same dosages and with administration routes as used herein before or about from 1 to 99% of the heretofore employed dosages.

An effective amount as used herein also includes an amount sufficient to delay the development of a symptom of the cancer, alter the course of a cancer (for example but not limited to, slow the progression of a symptom of the cancer, such as growth of a tumor), or reverse a symptom of the cancer or tumor. Thus, it is not possible to specify the exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dosage can vary depending upon the dosage form employed and the route of administration utilized. The dose ratio between toxic and therapeutic effects is the therapeutic index and can be expressed as the ratio $LD_{50}/ED_{50}$. Compositions and methods that exhibit large therapeutic indices are preferred. A therapeutically effective dose can be estimated initially from cell culture assays. Also, a dose can be formulated in animal models to achieve a circulating plasma concentration range that includes the $IC_{50}$, which achieves a half-maximal inhibition of symptoms as determined in cell culture, or in an appropriate animal model. Levels in plasma can be measured, for example, by high performance liquid chromatography. The effects of any particular dosage can be monitored by a suitable bioassay. The dosage can be determined by a physician and adjusted, as necessary, to suit observed effects of the treatment.

In various embodiments, the therapeutically or prophylactically effective amount of a compound of Formula I, I, III, IV or V for use with the methods described herein is any one or more of about 0.01 to 0.05 µg/kg/day, 0.05-0.1 µg/kg/day, 0.1 to 0.5 µg/kg/day, 0.5 to 5 µg/kg/day, 0.5 to 1 µg/kg/day, 1 to 5 µg/kg/day, 5 to 10 µg/kg/day, 10 to 20 µg/kg/day, 20 to 50 µg/kg/day, 50 to 100 µg/kg/day, 100 to 150 µg/kg/day, 150 to 200 µg/kg/day, 200 to 250 µg/kg/day, 250 to 300 µg/kg/day, 300 to 350 µg/kg/day, 350 to 400 µg/kg/day, 400 to 500 µg/kg/day, 500 to 600 µg/kg/day, 600 to 700 µg/kg/day, 700 to 800 µg/kg/day, 800 to 900 µg/kg/day, 900 to 1000 µg/kg/day, 0.01 to 0.05 mg/kg/day, 0.05-0.1 mg/kg/day, 0.1 to 0.5 mg/kg/day, 0.5 to 1 mg/kg/day, 1 to 5 mg/kg/day, 5 to 10 mg/kg/day, 10 to 15 mg/kg/day, 15 to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day, 900 to 1000 mg/kg/day or a combination thereof. Typical dosages of a compound of Formula I, I, III, IV or V can be in the ranges recommended by the manufacturer where known therapeutic compounds are used, and also as indicated to the skilled artisan by the in vitro responses or responses in animal models. Such dosages typically can be reduced by up to about an order of magnitude in concentration or amount without losing relevant biological activity. The actual dosage can depend upon the judgment of the physician, the condition of the patient, and the effectiveness of the therapeutic method based, for example, on the in vitro responsiveness of relevant cultured cells or histocultured tissue sample, such as biopsied malignant tumors, or the responses observed in the appropriate animal models. In various embodiments, a compound of Formula I, I, III, IV or V may be administered once a day (SID/QD), twice a day (BID), three times a day (TID), four times a day (QID), or more, so as to administer an effective amount to the subject, where the effective amount is any one or more of the doses described herein Depending on the type and severity of the disease, about 1 µg/kg to 100 mg/kg (e.g., 0.1-20 mg/kg) of a compound of Formula I, I, III, IV or V is an initial candidate dosage range for administration to the subject, whether, for example, by one or more separate administrations, or by continuous infusion. A typical daily dosage can range from about 1 µg/kg to about 100 mg/kg or more, depending on the factors mentioned above. For repeated administrations over several days or longer, depending on the condition, the treatment is sustained until the cancer is treated, as measured by the methods described above or known in the art. However, other dosage regimens can be useful. The progress of the therapeutic methods described herein is easily monitored by conventional techniques and assays, such as those described herein, or known to one of skill in the art. In other embodiments, such dosing regimen is used in combination with a chemotherapy regimen as the first line therapy for treating, inhibiting, reducing severity of, slowing progression of and/or preventing metastasis of locally recurrent or metastatic breast cancer.

The duration of the therapeutic methods described herein can continue for as long as medically indicated or until a desired therapeutic effect (e.g., those described herein) is achieved. In certain embodiments, administration of a compound of Formula I, II, III, IV or V is continued for at least 1 month, at least 2 months, at least 4 months, at least 6 months, at least 8 months, at least 10 months, at least 1 year, at least 2 years, at least 3 years, at least 4 years, at least 5 years, at least 10 years, at least 20 years, or for at least a period of years up to the lifetime of the subject.

The compounds of Formula I, II, III, IV or V can be administered to a subject, e.g., a human subject, in accordance with known methods, such as intravenous administration as a bolus or by continuous infusion over a period of time, by intramuscular, intraperitoneal, intracerebrospinal, subcutaneous, intra-articular, intrasynovial, intrathecal, oral, topical, or inhalation routes. Local administration can be used if, for example, extensive side effects or toxicity is associated with the administered compound. An ex vivo strategy can also be used for therapeutic applications.

Exemplary modes of administration include, but are not limited to, injection, infusion, inhalation (e.g., intranasal or intratracheal), ingestion, rectal, and topical (including buccal and sublingual) administration. The phrases "parenteral administration" and "administered parenterally" as used herein, refer to modes of administration other than enteral and topical administration, usually by injection. As used herein, "injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. The phrases "systemic administration," "administered systemically", "peripheral administration" and "administered peripherally" as used herein refer to the administration of a compound of Formula I, II, III, IV or V other than directly into a target site, tissue, or organ, such as the lung, such that it enters the subject's circulatory system and, thus, is subject to metabolism and other like processes.

In some embodiments, the compound of Formula I, II, III, IV or V is administered by intravenous infusion or injection. In some embodiments, where local treatment is desired, for example, at or near a site of a tumor, such as a tumor in the breast in a subject having breast cancer, the compound can be administered by intralesional administration. Additionally, in some embodiments, the compound can be administered by pulse infusion, particularly with declining doses of the compound. Preferably the dosing is given by injections, most preferably intravenous or subcutaneous injections, depending in part on whether the administration is brief or chronic.

In some embodiments, the compound of Formula I, II, III, IV or V is administered locally, e.g., by direct injections, when the disorder or location of the tumor permits, and the injections can be repeated periodically. The compound can also be delivered systemically to the subject or directly to the tumor cells, e.g., to a tumor or a tumor bed, following surgical excision of the tumor, in order to prevent or reduce local recurrence or metastasis, for example of a dormant tumor or micrometastases.

Therapeutic formulations of compounds of Formula I, II, III, IV or V can be prepared, in some aspects, by mixing the compound having the desired degree of purity with one or more pharmaceutically acceptable carriers, excipients or stabilizers (Remington's Pharmaceutical Sciences 16th edition, Osol, A. Ed. (1980)), in the form of lyophilized formulations or aqueous solutions. Such therapeutic formulations include formulation into pharmaceutical compositions or pharmaceutical formulations for parenteral administration, e.g., intravenous; mucosal, e.g., intranasal; enteral, e.g., oral; topical, e.g., transdermal; ocular, or other mode of administration.

As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent, media, encapsulating material, manufacturing aid (e.g., lubricant, talc magnesium, calcium or zinc stearate, or steric acid), or solvent encapsulating material, involved in maintaining the activity of, carrying, or transporting the compound of Formula I, II, III, IV or V, from one organ, or portion of the body, to another organ, or portion of the body.

Some non-limiting examples of acceptable carriers, excipients, or stabilizers that are nontoxic to recipients at the dosages and concentrations employed, include pH buffered solutions such as phosphate, citrate, and other organic acids; antioxidants, including ascorbic acid and methionine; lubricating agents, such as magnesium stearate, sodium lauryl sulfate and talc; excipients, such as cocoa butter and suppository waxes; oils, such as peanut oil, cottonseed oil, safflower oil, sesame oil, olive oil, corn oil and soybean oil; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, HDL, LDL, or immunoglobulins; hydrophilic polymers, such as polyvinylpyrrolidone; amino acids such as glycine, glutamine, asparagine, histidine, arginine, or lysine; monosaccharides, disaccharides, and other carbohydrates including mannose, starches (corn starch or potato starch), or dextrins; cellulose, and its derivatives, such as sodium carboxymethyl cellulose, methylcellulose, ethyl cellulose, microcrystalline cellulose and cellulose acetate; chelating agents such as EDTA; sugars such as sucrose, glucose, lactose, mannitol, trehalose or sorbitol; salt-forming counter-ions such as sodium; metal complexes (e.g. Zn-protein complexes); glycols, such as propylene glycol; polyols, such as glycerin; esters, such as ethyl oleate and ethyl laurate; agar; buffering agents, such as magnesium hydroxide and aluminum hydroxide; alginic acid; pyrogen-free water; isotonic saline; Ringer's solution; polyesters, polycarbonates and/or polyanhydrides; C2-C12 alcohols, such as ethanol; powdered tragacanth; malt; and/or non-ionic surfactants such as TWEEN™, PLURONICS™ or polyethylene glycol (PEG); and/or other non-toxic compatible substances employed in pharmaceutical formulations. Wetting agents, coloring agents, release agents, coating agents, sweetening agents, flavoring agents, perfuming agents, preservative and antioxidants can also be present in the formulation.

In some embodiments, the therapeutic formulation comprising a compound of Formula I, II, III, IV or V comprises a pharmaceutically acceptable salt, typically, e.g., sodium chloride, and preferably at about physiological concentrations. Optionally, the formulations described herein can contain a pharmaceutically acceptable preservative. In some embodiments, the preservative concentration ranges from 0.1 to 2.0%, typically v/v. Suitable preservatives include those known in the pharmaceutical arts. Benzyl alcohol, phenol, m-cresol, methylparaben, and propylparaben are examples of preservatives. Optionally, the formulations of the invention can include a pharmaceutically acceptable surfactant at a concentration of 0.005 to 0.02%.

In some embodiments of the aspects described herein, a compound of Formula I, II, III, IV or V can be specially formulated for administration of the compound to a subject in solid, liquid or gel form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, the compounds described herein, e.g., a compound of Formula I, II, III, IV or V, can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and 3,270,960. Examples of dosage forms include, but are not limited to: tablets; caplets; capsules, such as hard gelatin capsules and soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquids such as suspensions (e.g., aqueous or non-aqueous liquid suspensions, oil-in-water emulsions, or water-in-oil liquid emulsions), solutions, and elixirs; and sterile solids (e.g., crystalline or amorphous solids) that can be reconstituted to provide liquid dosage forms.

In some embodiments, parenteral dosage forms of the compound of Formula I, II, III, IV or V can be administered to a subject with a cancer or at increased risk for cancer by various routes, including, but not limited to, subcutaneous, intravenous (including bolus injection), intramuscular, and intraarterial. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, controlled-release parenteral dosage forms, and emulsions.

Suitable vehicles that can be used to provide parenteral dosage forms described herein are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

In some embodiments, the compound of Formula I, II, III, IV or V is formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington's Pharmaceutical Sciences, 18th ed., Mack Publishing, Easton, Pa. (1990).

Due to their ease of administration, tablets and capsules represent the most advantageous solid oral dosage unit forms, in which case solid pharmaceutical excipients are used. If desired, tablets can be coated by standard aqueous or nonaqueous techniques. These dosage forms can be prepared by any of the methods of pharmacy. In general, pharmaceutical compositions and dosage forms are prepared by uniformly and intimately admixing the active ingredient(s) with liquid carriers, finely divided solid carriers, or both, and then shaping the product into the desired presentation if necessary.

Typical oral dosage forms of the compositions are prepared by combining the pharmaceutically acceptable salt of a compound of Formula I, II, III, IV or V in an intimate admixture with at least one excipient according to conventional pharmaceutical compounding techniques. Excipients can take a wide variety of forms depending on the form of the composition desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, microcrystalline cellulose, kaolin, diluents, granulating agents, lubricants, binders, and disintegrating agents.

Binders suitable for use in the pharmaceutical formulations described herein include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical formulations described herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions described herein is typically present in from about 50 to about 99 weight percent of the pharmaceutical composition.

Disintegrants are used in the oral pharmaceutical formulations described herein to provide tablets that disintegrate when exposed to an aqueous environment. A sufficient amount of disintegrant that is neither too little nor too much to detrimentally alter the release of the active ingredient(s) should be used to form solid oral dosage forms of the compounds described herein. The amount of disintegrant used varies based upon the type of formulation, and is readily discernible to those of ordinary skill in the art. Disintegrants that can be used to form oral pharmaceutical formulations include, but are not limited to, agar, alginic acid, calcium carbonate, microcrystalline cellulose, croscarmellose sodium, crospovidone, polacrilin potassium, sodium starch glycolate, potato or tapioca starch, other starches, pre-gelatinized starch, clays, other algins, other celluloses, gums, and mixtures thereof.

Lubricants that can be used to form oral pharmaceutical formulations of the compound of Formula I, II, III, IV or V include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL® 200, manufactured by W. R. Grace Co. of Baltimore, Md.), a coagulated aerosol of synthetic silica (marketed by Degussa Co. of Plano, Tex.), CAB-O-SIL® (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

In other embodiments, lactose-free pharmaceutical formulations and dosage forms are provided, wherein such compositions preferably contain little, if any, lactose or other mono- or di-saccharides. As used herein, the term "lactose-free" means that the amount of lactose present, if any, is insufficient to substantially increase the degradation rate of an active ingredient. Lactose-free compositions of the disclosure can comprise excipients which are well known in the art and are listed in the USP (XXI)/NF (XVI), which is incorporated herein by reference.

The oral formulations of the compound of Formula I, II, III, IV or V further encompass, in some embodiments, anhydrous pharmaceutical compositions and dosage forms comprising the compound as active ingredients, since water can facilitate the degradation of some compounds. For example, the addition of water (e.g., 5%) is widely accepted in the pharmaceutical arts as a means of simulating long-term storage in order to determine characteristics such as shelf life or the stability of formulations over time. See, e.g., Jens T. Carstensen, Drug Stability: Principles & Practice, 379-80 (2nd ed., Marcel Dekker, NY, N.Y.: 1995). Anhydrous pharmaceutical compositions and dosage forms described herein can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected. Anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials) with or without desiccants, blister packs, and strip packs.

The compound of Formula I, II, III, IV or V can be administered directly to the airways in the form of an aerosol or by nebulization. Accordingly, for use as aerosols, in some embodiments, the compound can be packaged in a pressurized aerosol container together with suitable propellants, for example, hydrocarbon propellants like propane, butane, or isobutane with conventional adjuvants. In other embodiments, the compound can be administered in a non-pressurized form such as in a nebulizer or atomizer.

The term "nebulization" is well known in the art to include reducing liquid to a fine spray. Preferably, by such nebulization small liquid droplets of uniform size are produced from a larger body of liquid in a controlled manner. Nebulization can be achieved by any suitable means, including by using many nebulizers known and marketed today. As is well known, any suitable gas can be used to apply pressure during the nebulization, with preferred gases being those which are chemically inert to the compound. Exemplary gases include, but are not limited to, nitrogen, argon or helium.

In other embodiments, the compound of Formula I, II, III, IV or V can be administered directly to the airways in the form of a dry powder. For use as a dry powder, the compound can be administered by use of an inhaler. Exemplary inhalers include metered dose inhalers and dry powdered inhalers.

Suitable powder compositions include, by way of illustration, powdered preparations of a compound of Formula I, II, III, IV or V thoroughly intermixed with lactose, or other inert powders acceptable for, e.g., intrabronchial administration. The powder compositions can be administered via an aerosol dispenser or encased in a breakable capsule which may be inserted by the subject into a device that punctures the capsule and blows the powder out in a steady stream suitable for inhalation. The compositions can include propellants, surfactants, and co-solvents and may be filled into conventional aerosol containers that are closed by a suitable metering valve.

Aerosols for the delivery to the respiratory tract are known in the art. See for example, Adjei, A. and Garren, J. Pharm. Res., 1: 565-569 (1990); Zanen, P. and Lamm, J.-W. J. Int. J. Pharm., 114: 111-115 (1995); Gonda, I. "Aerosols for delivery of therapeutic and diagnostic agents to the respiratory tract," in Critical Reviews in Therapeutic Drug Carrier Systems, 6:273-313 (1990); Anderson et al., Am. Rev. Respir. Dis., 140: 1317-1324 (1989)) and have potential for the systemic delivery of peptides and proteins as well (Patton and Platz, Advanced Drug Delivery Reviews, 8:179-196 (1992)); Timsina et al., Int. J. Pharm., 101: 1-13 (1995); and Tansey, I. P., Spray Technol. Market, 4:26-29 (1994); French, D. L., Edwards, D. A. and Niven, R. W., Aerosol Sci., 27: 769-783 (1996); Visser, J., Powder Technology 58: 1-10 (1989)); Rudt, S. and R. H. Muller, J. Controlled Release, 22: 263-272 (1992); Tabata, Y, and Y. Ikada, Biomed. Mater. Res., 22: 837-858 (1988); Wall, D. A., Drug Delivery, 2: 10 1-20 1995); Patton, J. and Platz, R., Adv. Drug Del. Rev., 8: 179-196 (1992); Bryon, P., Adv. Drug. Del. Rev., 5: 107-132 (1990); Patton, J. S., et al., Controlled Release, 28: 15 79-85 (1994); Damms, B. and Bains, W., Nature Biotechnology (1996); Niven, R. W., et al., Pharm. Res., 12(9); 1343-1349 (1995); and Kobayashi, S., et al., Pharm. Res., 13(1): 80-83 (1996), contents of all of which are herein incorporated by reference in their entirety.

Topical dosage forms of the compound of Formula I, II, III, IV or V are also provided in some embodiments, and include, but are not limited to, creams, lotions, ointments, gels, shampoos, sprays, aerosols, solutions, emulsions, and other forms known to one of skill in the art. See, e.g., Remington's Pharmaceutical Sciences, 18th ed., Mack Publishing, Easton, Pa. (1990); and Introduction to Pharmaceutical Dosage Forms, 4th ed., Lea & Febiger, Philadelphia, Pa. (1985). For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as Freon), or in a squeeze bottle. Moisturizers or humectants can also be added to pharmaceutical compositions and dosage forms if desired. Examples of such additional ingredients are well known in the art. See, e.g., Remington's Pharmaceutical Sciences, 18.sup.th Ed., Mack Publishing, Easton, Pa. (1990) and Introduction to Pharmaceutical Dosage Forms, 4th Ed., Lea & Febiger, Philadelphia, Pa. (1985). Dosage forms suitable for treating mucosal tissues within the oral cavity can be formulated as mouthwashes, as oral gels, or as buccal patches. Additional transdermal dosage forms include "reservoir type" or "matrix type" patches, which can be applied to the skin and worn for a specific period of time to permit the penetration of a desired amount of active ingredient.

Examples of transdermal dosage forms and methods of administration that can be used to administer a compound of Formula I, II, III, IV or V include, but are not limited to, those disclosed in U.S. Pat. Nos. 4,624,665; 4,655,767; 4,687,481; 4,797,284; 4,810,499; 4,834,978; 4,877,618; 4,880,633; 4,917,895; 4,927,687; 4,956,171; 5,035,894; 5,091,186; 5,163,899; 5,232,702; 5,234,690; 5,273,755; 5,273,756; 5,308,625; 5,356,632; 5,358,715; 5,372,579; 5,421,816; 5,466,465; 5,494,680; 5,505,958; 5,554,381; 5,560,922; 5,585,111; 5,656,285; 5,667,798; 5,698,217; 5,741,511; 5,747,783; 5,770,219; 5,814,599; 5,817,332; 5,833,647; 5,879,322; and 5,906,830, each of which are incorporated herein by reference in their entirety.

Suitable excipients (e.g., carriers and diluents) and other materials that can be used to provide transdermal and mucosal dosage forms of the inhibitors described herein are well known to those skilled in the pharmaceutical arts, and depend on the particular tissue or organ to which a given pharmaceutical composition or dosage form will be applied.

In addition, depending on the specific tissue to be treated, additional components may be used prior to, in conjunction with, or subsequent to treatment with a compound of Formula I, II, III, IV or V. For example, penetration enhancers can be used to assist in delivering the active ingredients to or across the tissue.

In some embodiments of the aspects described herein, the pharmaceutical formulations comprising the compound of Formula I, II, III, IV or V can further comprise more than one active compound as necessary for the particular indication being treated, preferably those with complementary activities that do not adversely affect each other. For example, in some embodiments, it can be desirable to further provide antibodies which bind to EGFR, VEGF, VEGFR, or ErbB2 (e.g., Herceptin™) in the formulation comprising the compound of Formula I, II, III, IV or V. In other embodiments, the formulation comprising the compound of Formula I, II, III, IV or can comprise a cytotoxic agent, cytokine, growth inhibitory agent and/or VEGFR antagonist. Such molecules are suitably present in combination in amounts that are effective for the purpose intended.

In some embodiments, the active ingredients of the formulations comprising the compound of Formula I, II, III, IV or V can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

In some embodiments of these aspects, the compound of Formula I, II, III, IV or V can be administered to a subject by controlled- or delayed-release means. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. (Kim, Cherng-ju, Controlled Release Dosage Form Design, 2 (Technomic Publishing, Lancaster, Pa.: 2000)). Controlled-release formulations can be used to control the compound's duration of action, plasma levels within the therapeutic window, and peak blood levels. In particular, controlled- or extended-release dosage forms or formulations can be used to ensure that the maximum effectiveness of the compound of Formula I, II, III, IV or V is achieved while minimizing potential adverse effects and safety concerns, which can occur both from under-dosing a drug (i.e., going below the minimum therapeutic levels) as well as exceeding the toxicity level for the drug.

A variety of known controlled- or extended-release dosage forms, formulations, and devices can be adapted for use with the compounds of Formula I, II, III, IV or V. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated ins entirety herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed salt forms of the disclosed compounds and thus effect controlled delivery of the drug. Examples of specific anion exchangers include, but are not limited to, Duolite® A568 and Duolite® AP143 (Rohm & Haas, Spring House, Pa. USA).

In some embodiments of the various aspects described herein, the compound of Formula I, II, III, IV or V is administered to a subject by sustained release or in pulses. Pulse therapy is not a form of discontinuous administration of the same amount of a composition over time, but comprises administration of the same dose of the composition at a reduced frequency or administration of reduced doses. Sustained release or pulse administrations are particularly preferred in chronic conditions, such as cancer, as each pulse dose can be reduced and the total amount of the compound administered over the course of treatment to the patient is minimized.

The interval between pulses, when necessary, can be determined by one of ordinary skill in the art. Often, the interval between pulses can be calculated by administering another dose of the composition when the composition or the active component of the composition is no longer detectable in the subject prior to delivery of the next pulse. Intervals can also be calculated from the in vivo half-life of the composition. Intervals may be calculated as greater than the in vivo half-life, or 2, 3, 4, 5 and even 10 times greater the composition half-life. Various methods and apparatus for pulsing compositions by infusion or other forms of delivery to the patient are disclosed in U.S. Pat. Nos. 4,747,825; 4,723,958; 4,948,592; 4,965,251 and 5,403,590.

In some embodiments, sustained-release preparations comprising the compound of Formula I, II, III, IV or V can be prepared. Suitable examples of sustained-release preparations include semipermeable matrices of solid hydrophobic polymers containing the compound, in which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations comprising the compound of Formula I, II, III, IV or V to be used for in vivo administration are preferably sterile. This is readily accomplished by filtration through, for example, sterile filtration membranes, and other methods known to one of skill in the art.

One key advantage of the methods, uses and compositions comprising the compound of Formula I, II, III, IV or V is the ability of producing marked anti-cancer effects in a human subject without causing significant toxicities or adverse effects. The efficacy of the treatments described herein can be measured by various parameters commonly used in evaluating cancer treatments, including but not limited to, tumor regression, tumor weight or size shrinkage, reduction in rate of tumor growth, the presence or the size of a dormant tumor, the presence or size of metastases or micrometastases, degree of tumor or cancer invasiveness, size or number of the blood vessels, time to progression, duration of survival, progression free survival, overall response rate, duration of response, and quality of life. For example, tumor shrinkage of greater than 50% in a 2-dimensional analysis is the standard cut-off for declaring a response. However, in some embodiments, the compositions comprising the compound of Formula I, II, III, IV or V can be used to cause inhibition of metastatic spread without shrinkage of the primary tumor, or can simply exert a tumoristatic effect. In the case of cancers, the therapeutically effective amount of the compositions comprising the compound of Formula I, II, III, IV or V can reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the compositions comprising the compound of Formula I, II, III, IV or V can prevent growth and/or kill existing cancer cells, it can be cytostatic and/or cytotoxic. For cancer therapy, efficacy in vivo can, for example, be measured by assessing the duration of survival, duration of progression free survival (PFS), the response rates (RR), duration of response, and/or quality of life.

In some embodiments, methods for increasing progression free survival of a human subject susceptible to or diagnosed with a cancer are described herein. "Time to disease progression," as used herein, is defined as the time from administration of the drug until disease progression or death. In a preferred embodiments, the method of treatments described herein using the compound of Formula I, II, III, IV or V, and, in some further embodiments, one or more chemotherapeutic agents, significantly increases progression free survival by at least about 1 month, at least about 2 months, at least about 3 months, at least about 4 months, at least about 5 months, at least about 6 months, at least about 7 months, at least about 8 months, at least about 9 months, at least about 10 months, at least about 11 months, when compared to no treatment or a treatment with chemotherapy alone.

In other embodiments, the methods of treatment described herein significantly increase response rate in a group of human subjects susceptible to or diagnosed with a cancer who are treated with various therapeutics. "Response rate," as used herein, is defined as the percentage of treated subjects who responded to the treatment. In some such embodiments, the combination treatments described herein comprising using a compound of Formula I, II, III, IV or V and, in some further embodiments, one or more chemotherapeutic agents, significantly increases response rate in the treated subject group compared to an untreated group or a group treated with chemotherapy alone.

In other embodiments of these methods, the administration of a compound of Formula I, II, III, IV or V is used for increasing duration of response in a human subject or a group of human subjects susceptible to or diagnosed with a cancer. As used herein, "duration of response" is defined as the time from the initial response to disease progression. In some such embodiments, the compound of Formula I, II, III, IV or V can be used for increasing the duration of survival of a human subject susceptible to or diagnosed with a cancer.

As used herein, the terms "treat," "treatment," "treating," or "amelioration" refer to therapeutic treatments, wherein the object is to reverse, alleviate, ameliorate, inhibit, slow down or stop the progression or severity of a condition associated with, a disease or disorder. The term "treating" includes reducing or alleviating at least one adverse effect or symptom of a condition, disease or disorder associated with a chronic immune condition, such as, but not limited to, a chronic infection or a cancer. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. The term "treatment" of a disease also includes providing relief from the symptoms or side-effects of the disease (including palliative treatment).

For example, in some embodiments, the methods described herein comprise administering an effective amount of the compound of Formula I, II, III, IV or V to a subject in order to alleviate a symptom of a cancer, or other such disorder. As used herein, "alleviating a symptom of a cancer" is ameliorating or reducing any condition or symptom associated with the cancer. As compared with an equivalent untreated control, such reduction or degree of prevention is at least 5%, 10%, 20%, 40%, 50%, 60%, 80%, 90%, 95%, or 100% as measured by any standard technique. Ideally, the cancer is completely cleared as detected by any standard method known in the art, in which case the cancer is considered to have been treated. A patient who is being treated for a cancer is one who a medical practitioner has diagnosed as having such a condition. Diagnosis can be by any suitable means. Diagnosis and monitoring can involve, for example, detecting the level of cancer cells in a biological sample (for example, a tissue or lymph node biopsy, blood test, or urine test), detecting the level of a surrogate marker of the cancer in a biological sample, detecting symptoms associated with the specific cancer, or detecting immune cells involved in the immune response typical of such a cancer infections.

In some embodiments, the compositions and methods comprising the compound of Formula I, II, III, IV or V further comprise administration or treatment with one or more additional cancer therapies. Examples of anti-cancer therapies include, without limitation, surgery, radiation therapy (radiotherapy), biotherapy, immunotherapy, chemotherapy, or a combination of these therapies. In addition, cytotoxic agents, anti-angiogenic and anti-proliferative agents can be used in combination with the compounds of Formula I, II, III, IV or V.

For the treatment of cancer in such embodiments comprising combination therapies, the appropriate dosage of a compound of Formula I, II, III, IV or V will depend on the type of disease to be treated, as defined above, the severity and course of the disease, whether the compound is administered for preventive or therapeutic purposes, previous therapy, the subject's clinical history and response to the compound, and the discretion of the attending physician. The compound can be suitably administered to the subject at one time or over a series of treatments.

In those embodiments where a combination therapy regimen is applied, the compound of Formula I, II, III, IV or V and one or more anti-cancer therapeutic agents as described herein are administered in a therapeutically effective or synergistic amount. As used in such embodiments encompassing combination therapies, a therapeutically effective amount is such that co-administration of the compound of Formula I, II, III, IV or V, and one or more other therapeutic agents, or administration of a therapeutic composition or formulation comprising a compound of Formula I, II, III, IV or V, results in reduction or inhibition of the cancer as described herein. A "therapeutically synergistic amount" is that amount of the compound of Formula I, II, III, IV or V, and one or more other therapeutic agents necessary to synergistically or significantly reduce or eliminate conditions or symptoms associated with a particular cancer.

In some embodiments, a compound of Formula I, II, III, IV or V, and one or more other therapeutic agents can be administered simultaneously or sequentially in an amount and for a time sufficient to reduce or eliminate the occurrence or recurrence of a tumor, a dormant tumor, or a micrometastases. In some embodiments, the compound of Formula I, II, III, IV or V, and one or more other therapeutic agents can be administered as maintenance therapy to prevent or reduce the likelihood of recurrence of the tumor.

As will be understood by those of ordinary skill in the art, the appropriate doses of chemotherapeutic agents or other anti-cancer agents will be generally around those already employed in clinical therapies, e.g., where the chemotherapeutics are administered alone or in combination with other chemotherapeutics. Variation in dosage will likely occur depending on the condition being treated. The physician administering treatment will be able to determine the appropriate dose for the individual subject.

In addition to the above therapeutic regimes, the subject can be subjected to radiation therapy.

The term "anti-cancer therapy" refers to a therapy useful in treating, inhibiting, reducing severity of, slowing progression of and/or preventing metastasis of cancer. Examples of anti-cancer therapeutic agents include, but are limited to, e.g., surgery, radiation therapy, chemotherapeutic agents, growth inhibitory agents, cytotoxic agents, agents used in radiation therapy, anti-angiogenesis agents, apoptotic agents, anti-tubulin agents, and other agents to treat cancer, such as anti-HER-2 antibodies (e.g., Herceptin™), anti-CD20 antibodies, an epidermal growth factor receptor (EGFR) antagonist (e.g., a tyrosine kinase inhibitor), HER1/EGFR inhibitor (e.g., erlotinib (Tarceva™), platelet derived growth factor inhibitors (e.g., Gleevec™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also included in the embodiments described herein.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{186}$, $sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

As used herein, a "chemotherapeutic agent" is a chemical compound useful in the treatment of cancer. Examples of chemotherapeutic agents include, but are not limited to, alkylating agents such as thiotepa and CYTOXAN™ cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma II and calicheamicin omegaII (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN™, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK™, polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL™, paclitaxel (Bristol-Myers Squibb Oncology, Princeton, N.J.), ABRAXANE™, Cremophor-free, albumin-engineered nanoparticle formulation of paclitaxel (American Pharmaceutical Partners, Schaumberg, Ill.), and TAXOTERE™, doxetaxel (Rhone-Poulenc Rorer, Antony, France); chloranbucil; GEMZAR™ gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb™); inhibitors of PKC-alpha, Raf, H-Ras, EGFR (e.g., erlotinib (Tarceva™.)) and VEGF-A that reduce cell proliferation and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen (including NOLVADEX™ tamoxifen), raloxifene, droloxifene, 4-hydroxytamoxifen, trioxifene, keoxifene, LY117018, onapristone, and FARESTON toremifene; aromatase inhibitors that inhibit the enzyme aromatase, which regulates estrogen production in the adrenal glands, such as, for example, 4(5)-imidazoles, aminoglutethimide, MEGASE™ megestrol acetate, AROMASIN™ exemestane, formestanie, fadrozole, RIVISOR™ vorozole, FEMARA™ letrozole, and ARIMIDEX™ anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in aberrant cell proliferation, such as, for example, PKC-alpha, Ralf and H-Ras; ribozymes such as a VEGF expression inhibitor (e.g., ANGIOZYME™ ribozyme) and a HER2 expression inhibitor; vaccines such as gene therapy vaccines, for example, ALLOVECTIN™ vaccine, LEUVECTIN™ vaccine, and VAXID™ vaccine; PROLEUKIN™ rIL-2; LURTOTECAN™ topoisomerase 1 inhibitor; ABARELIX™ rmRH; and pharmaceutically acceptable salts, acids or derivatives of any of the above.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); epidermal growth factor; hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-alpha; platelet-growth factor; transforming growth factors (TGFs) such as TGF-alpha and TGF-beta; insulin-like growth factor-I and -II; erythropoietin (EPO); osteoinductive factors; interferons such as interferon-alpha, -beta and -gamma colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; a tumor necrosis factor such as TNF-alpha or TNF-beta; and other polypeptide factors including LIF and kit ligand (KL). As used herein, the term cytokine includes proteins from natural sources or from recombinant cell culture and biologically active equivalents of the native sequence cytokines.

A "growth inhibitory agent" when used herein refers to a compound or composition which inhibits growth of a cell in vitro and/or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), TAXOL™, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (WB Saunders: Philadelphia, 1995), especially p. 13.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one time administration and typical dosages range from 10 to 200 units (Grays) per day.

Some Selected Definitions

For convenience, certain terms employed herein, in the specification, examples and appended claims are collected herein. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology, and molecular biology can be found in The Merck Manual of Diagnosis and Therapy, 18th Edition, published by Merck Research Laboratories, 2006 (ISBN 0-911910-18-2); Robert S. Porter et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006. Definitions of common terms in molecular biology are found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl Eds., Academic Press Inc., San Diego, USA (1987); Current Protocols in Molecular Biology (CPMB) (Fred M. Ausubel, et al. ed., John Wiley and Sons, Inc.), Current Protocols in Protein Science (CPPS) (John E. Coligan, et. al., ed., John Wiley and Sons, Inc.) and Current Protocols in Immunology (CPI) (John E. Coligan, et. al., ed. John Wiley and Sons, Inc.), which are all incorporated by reference herein in their entireties.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

The singular terms "a," "an," and "the" include plural referents unless context clearly indicates otherwise. Similarly, the word "or" is intended to include "and" unless the context clearly indicates otherwise.

Other than in the operating examples, or where otherwise indicated, all numbers expressing quantities of ingredients or reaction conditions used herein should be understood as modified in all instances by the term "about." The term "about" when used in connection with percentages may mean±5% of the value being referred to. For example, about 100 means from 95 to 105. In some embodiments, the term "about" when used in connection with percentages may mean±1% of the value being referred to Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means at least two standard deviation (2SD) away from a reference level. The term refers to statistical evidence that there is a difference. It is defined as the probability of making a decision to reject the null hypothesis when the null hypothesis is actually true.

The term "modulate" in reference to a RelA modulator is used consistently with its use in the art, e.g., meaning to cause or facilitate a qualitative or quantitative change, alteration, or modification in one or more biological processes, mechanisms, effects, responses, functions, activities, pathways, or other phenomena of interest. Accordingly, as used herein, modulate refers to a qualitative or quantitative change, alteration, or modification in one or more processes, mechanisms, effects, responses, functions, activities or pathways mediated by RelA.

As used herein, the term "RelA modulator" refers to an agent that causes or facilitates a qualitative or quantitative change, alteration, or modification in one or more processes, mechanisms, effects, responses, functions, activities or pathways mediated by the RelA. Such changes mediated by an RelA modulator, such as an inhibitor of the RelA described herein, can refer to a decrease or an increase in the activity or function of the RelA, such as a decrease in, inhibition of, or diversion of, constitutive activity of the RelA. The terms "inhibitor of RelA" or "RelA inhibitor" refers to an agent or compound that inhibits one or more constitutive activity of RelA. For example, but not limited to, DNA binding activity of RelA.

The terms "subject" and "individual" are used interchangeably herein, and mean a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient" and "subject" are used interchangeably herein. The terms, "patient" and "subject" are used interchangeably herein.

Preferably, the subject is a mammal. The mammal can be a human, non-human primate, mouse, rat, dog, cat, horse, or cow, but are not limited to these examples. Mammals other than humans can be advantageously used as subjects that represent animal models of PH, PAH, or fibrotic or fibroproliferative disease.

In addition, the methods described herein can be used to treat domesticated animals and/or pets. Without limitations, a subject can be male or female.

The terms "cancer" and "cancerous" refer to or describe the physiological condition in mammals that is typically characterized by unregulated cell growth or proliferation, which interferes with the normal functioning of the bodily organs and systems. Accordingly, the terms "cancer" or "tumor" as used herein refers to an uncontrolled growth of cells which interferes with the normal functioning of the bodily organs and systems, including cancer stem cells and tumor vascular niches. A subject that has a cancer or a tumor is a subject having objectively measurable cancer cells present in the subject's body. Cancers which migrate from their original location and seed vital organs can eventually lead to the death of the subject through the functional deterioration of the affected organs. Hematopoietic cancers, such as leukemia, are able to out-compete the normal hematopoietic compartments in a subject, thereby leading to hematopoietic failure (in the form of anemia, thrombocytopenia and neutropenia) ultimately causing death. Included in this definition are benign and malignant cancers, as well as dormant tumors or micrometastatses.

A "metastasis" refers to the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass. Both stimulatory and inhibitory molecular pathways within the tumor cell regulate this behavior, and interactions between the tumor cell and host cells in the distant site are also significant.

Metastases are most often detected through the sole or combined use of magnetic resonance imaging (MRI) scans, computed tomography (CT) scans, blood and platelet counts, liver function studies, chest X-rays and bone scans in addition to the monitoring of specific symptoms.

Accordingly, cancers that can be treated using the compositions and methods described in the various aspects herein include, but are not limited to, carcinoma, lymphoma, blastoma, sarcoma, and leukemia. More particular examples of such cancers include, but are not limited to, breast cancer; basal cell carcinoma, biliary tract cancer; bladder cancer; bone cancer; brain and CNS cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; glioblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

In some embodiments, a cancer can be a solid tumor. As used herein, a "solid tumor" refers to an abnormal mass of tissue that usually does not contain cysts or liquid areas. Solid tumors can be benign or malignant. Different types of solid tumors are named for the type of cells that form them. Non-limiting examples of solid tumors are sarcomas, carcinomas, and lymphomas. Leukemias and other cancers of the blood generally do not form solid tumors and are not hence encompassed by the term 'solid tumor' as used herein.

In some embodiments, cancer is breast cancer. In some further embodiments, cancer is triple negative breast cancer. Triple-negative breast cancer refers to any breast cancer that does not express the genes for estrogen receptor (ER), progesterone receptor (PR) or Her2/neu. This makes it more difficult to treat since most chemotherapies target one of the three receptors, so triple-negative cancers often require combinatorial therapies. Triple negative is sometimes used as a surrogate term for basal-like; however, more detailed classification may provide better guidance for treatment and better estimates for prognosis.

Triple-negative breast cancers comprise a very heterogeneous group of cancers. There is conflicting information over prognosis for the various subtypes but it appears that the Nottingham prognostic index is valid and hence general prognosis is rather similar with other breast cancer of same stage, except that more aggressive treatment is required. Some types of triple-negative breast cancer are known to be more aggressive with poor prognosis, while other types have prognosis very similar or better than hormone receptor positive breast cancers. Pooled data of all triple-negative subtypes suggest that with optimal treatment 20-year survival rates are very close to those of hormone positive cancer.

Triple-negative breast cancers have a relapse pattern that is very different from hormone-positive breast cancers: the risk of relapse is much higher for the first 3-5 years but drops sharply and substantially below that of hormone-positive breast cancers after that. This relapse pattern has been recognized for all types of triple-negative cancers for which sufficient data exists although the absolute relapse and survival rates differ across subtypes.

Triple-negative breast cancers are sometimes classified into "basal-type" and other cancers. However, there is no standard classification scheme. Basal type cancers are frequently defined by cytokeratin 5/6 and EGFR staining. However, no clear criteria or cutoff values have been standardized yet. http://en.wikipedia.org/wiki/Tripie-negative_breast_cancer-cite_note-Hudis_2011-2About 75% of basal-type breast cancers are triple negative.

Some TNBC overexpresses epidermal growth factor receptor (EGFR). Some TNBC over expresses transmembrane glycoprotein NMB (GPNMB).

Upon histologic examination, triple-negative breast tumors mostly fall into the categories of secretory cell carcinoma or adenoid cystic types (both considered less aggressive); medullary cancers and grade 3 invasive ductal carcinomas with no specific subtype; and highly aggressive The term "anti-cancer therapy" refers to a therapy or therapeutic agent useful in treating, inhibiting, reducing severity of, slowing progression of and/or preventing metastasis of cancer. Examples of anti-cancer therapeutic agents include, but are limited to, e.g., surgery, chemotherapeutic agents, growth inhibitory agents, cytotoxic agents, agents used in radiation therapy, anti-angiogenesis agents, apoptotic agents, anti-tubulin agents, and other agents to treat cancer, such as anti-HER-2 antibodies (e.g., Herceptin™), anti-CD20 antibodies, an epidermal growth factor receptor (EGFR) antagonist (e.g., a tyrosine kinase inhibitor), HER1/EGFR inhibitor (e.g., erlotinib (Tarceva™), platelet derived growth factor inhibitors (e.g., Gleevec™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, PARP inhibitors, HDAC inhibitors and other bioactive and organic chemical agents, etc. Combinations thereof are also included in the embodiments described herein.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "aliphatic" means a moiety characterized by a straight or branched chain arrangement of constituent carbon atoms and can be saturated or partially unsaturated with one or more (e.g., one, two, three, four, five or more) double or triple bonds.

As used herein, the term "alicyclic" means a moiety comprising a nonaromatic ring structure. Alicyclic moieties can be saturated or partially unsaturated with one or more double or triple bonds. Alicyclic moieties can also optionally comprise heteroatoms such as nitrogen, oxygen and sulfur. The nitrogen atoms can be optionally quaternerized or oxidized and the sulfur atoms can be optionally oxidized. Examples of alicyclic moieties include, but are not limited to moieties with $C_3$-$C_8$ rings such as cyclopropyl, cyclohexane, cyclopentane, cyclopentene, cyclopentadiene, cyclohexane, cyclohexene, cyclohexadiene, cycloheptane, cycloheptene, cycloheptadiene, cyclooctane, cyclooctene, and cyclooctadiene.

As used herein, the term "alkyl" means a straight or branched, saturated aliphatic radical having a chain of carbon atoms. $C_x$ alkyl and $C_x$-$C_y$alkyl are typically used where X and Y indicate the number of carbon atoms in the chain. For example, $C_1$-$C_6$alkyl includes alkyls that have a chain of between 1 and 6 carbons (e.g., methyl, ethyl, propyl, isopropyl, butyl, sec-butyl, isobutyl, tert-butyl, pentyl, neopentyl, hexyl, and the like). Alkyl represented along with another radical (e.g., as in arylalkyl) means a straight or branched, saturated alkyl divalent radical having the number of atoms indicated or when no atoms are indicated means a bond, e.g., ($C_6$-$C_{10}$)aryl($C_0$-$C_3$)alkyl includes phenyl, benzyl, phenethyl, 1-phenylethyl 3-phenylpropyl, and the like. Backbone of the alkyl can be optionally inserted with one or more heteroatoms, such as N, O, or S.

In preferred embodiments, a straight chain or branched chain alkyl has 30 or fewer carbon atoms in its backbone (e.g., C1-C30 for straight chains, C3-C30 for branched chains), and more preferably 20 or fewer. Likewise, preferred cycloalkyls have from 3-10 carbon atoms in their ring structure, and more preferably have 5, 6 or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

Substituents of a substituted alkyl can include halogen, hydroxy, nitro, thiols, amino, azido, imino, amido, phosphoryl (including phosphonate and phosphinate), sulfonyl (including sulfate, sulfonamide, sulfamoyl and sulfonate), and silyl groups, as well as ethers, alkylthios, carbonyls (including ketones, aldehydes, carboxylates, and esters), —CF3, —CN and the like.

As used herein, the term "alkenyl" refers to unsaturated straight-chain, branched-chain or cyclic hydrocarbon radicals having at least one carbon-carbon double bond. $C_x$ alkenyl and $C_x$-$C_y$alkenyl are typically used where X and Y indicate the number of carbon atoms in the chain. For example, $C_2$-$C_6$alkenyl includes alkenyls that have a chain of between 1 and 6 carbons and at least one double bond, e.g., vinyl, allyl, propenyl, isopropenyl, 1-butenyl, 2-butenyl, 3-butenyl, 2-methylallyl, 1-hexenyl, 2-hexenyl, 3-hexenyl, and the like). Alkenyl represented along with another radical (e.g., as in arylalkenyl) means a straight or branched, alkenyl divalent radical having the number of atoms indicated. Backbone of the alkenyl can be optionally inserted with one or more heteroatoms, such as N, O, or S.

As used herein, the term "alkynyl" refers to unsaturated hydrocarbon radicals having at least one carbon-carbon triple bond. $C_x$ alkynyl and $C_x$-$C_y$alkynyl are typically used where X and Y indicate the number of carbon atoms in the chain. For example, $C_2$-$C_6$alkynyl includes alkynls that have a chain of between 1 and 6 carbons and at least one triple bond, e.g., ethynyl, 1-propynyl, 2-propynyl, 1-butynyl, isopentynyl, 1,3-hexa-diyn-yl, n-hexynyl, 3-pentynyl, 1-hexen-3-ynyl and the like. Alkynyl represented along with another radical (e.g., as in arylalkynyl) means a straight or branched, alkynyl divalent radical having the number of atoms indicated. Backbone of the alkynyl can be optionally inserted with one or more heteroatoms, such as N, O, or S.

The terms "alkylene," "alkenylene," and "alkynylene" refer to divalent alkyl, alkelyne, and alkynylene" radicals. Prefixes $C_x$ and $C_x$-$C_y$ are typically used where X and Y indicate the number of carbon atoms in the chain. For example, $C_1$-$C_6$alkylene includes methylene, (—$CH_2$—), ethylene (—$CH_2CH_2$—), trimethylene (—$CH_2CH_2CH_2$—), tetramethylene (—$CH_2CH_2CH_2CH_2$—), 2-methyltetramethylene (—$CH_2CH(CH_3)CH_2CH_2$—), pentamethylene (—$CH_2CH_2CH_2CH_2CH_2$—) and the like).

As used herein, the term "alkylidene" means a straight or branched unsaturated, aliphatic, divalent radical having a general formula =CR$_a$R$_b$. C$_x$ alkylidene and C$_x$-C$_y$alkylidene are typically used where X and Y indicate the number of carbon atoms in the chain. For example, C$_2$-C$_6$alkylidene includes methylidene (=CH$_2$), ethylidene (=CHCH$_3$), isopropylidene (=C(CH$_3$)$_2$), propylidene (=CHCH$_2$CH$_3$), allylidene (=CH—CH=CH$_2$), and the like).

The term "heteroalkyl", as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

As used herein, the term "halogen" or "halo" refers to an atom selected from fluorine, chlorine, bromine and iodine. The term "halogen radioisotope" or "halo isotope" refers to a radionuclide of an atom selected from fluorine, chlorine, bromine and iodine.

A "halogen-substituted moiety" or "halo-substituted moiety", as an isolated group or part of a larger group, means an aliphatic, alicyclic, or aromatic moiety, as described herein, substituted by one or more "halo" atoms, as such terms are defined in this application. For example, halo-substituted alkyl includes haloalkyl, dihaloalkyl, trihaloalkyl, perhaloalkyl and the like (e.g. halosubstituted (C$_1$-C$_3$)alkyl includes chloromethyl, dichloromethyl, difluoromethyl, trifluoromethyl (—CF$_3$), 2,2,2-trifluoroethyl, perfluoroethyl, 2,2,2-trifluoro-1,1-dichloroethyl, and the like).

The term "aryl" refers to monocyclic, bicyclic, or tricyclic fused aromatic ring system. C$_x$ aryl and C$_x$-C$_y$aryl are typically used where X and Y indicate the number of carbon atoms in the ring system. Exemplary aryl groups include, but are not limited to, pyridinyl, pyrimidinyl, furanyl, thienyl, imidazolyl, thiazolyl, pyrazolyl, pyridazinyl, pyrazinyl, triazinyl, tetrazolyl, indolyl, benzyl, phenyl, naphthyl, anthracenyl, azulenyl, fluorenyl, indanyl, indenyl, naphthyl, phenyl, tetrahydronaphthyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl, and the like. In some embodiments, 1, 2, 3, or 4 hydrogen atoms of each ring can be substituted by a substituent.

The term "heteroaryl" refers to an aromatic 5-8 membered monocyclic, 8-12 membered fused bicyclic, or 11-14 membered fused tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively. C$_x$ heteroaryl and C$_x$-C$_y$heteroaryl are typically used where X and Y indicate the number of carbon atoms in the ring system. Heteroaryls include, but are not limited to, those derived from benzo[b]furan, benzo[b]thiophene, benzimidazole, imidazo[4,5-c]pyridine, quinazoline, thieno[2,3-c]pyridine, thieno[3,2-b]pyridine, thieno[2, 3-b]pyridine, indolizine, imidazo[1,2a]pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3]pyridine, pyrrolo[3,2-c]pyridine, pyrrolo[3,2-b]pyridine, pyrrolo[2,3-d]pyrimidine, pyrrolo[3,2-d]pyrimidine, pyrrolo[2,3-b]pyrazine, pyrazolo[1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, carbazole, acridine, phenazine, phenothiazene, phenoxazine, 1,2-dihydropyrrolo[3,2,1-hi]indole, indolizine, pyrido[1,2-a]indole, 2(1H)-pyridinone, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. Some exemplary heteroaryl groups include, but are not limited to, pyridyl, furyl or furanyl, imidazolyl, benzimidazolyl, pyrimidinyl, thiophenyl or thienyl, pyridazinyl, pyrazinyl, quinolinyl, indolyl, thiazolyl, naphthyridinyl, 2-amino-4-oxo-3,4-dihydropteridin-6-yl, tetrahydroisoquinolinyl, and the like. In some embodiments, 1, 2, 3, or 4 hydrogen atoms of each ring may be substituted by a substituent.

The term "cyclyl" or "cycloalkyl" refers to saturated and partially unsaturated cyclic hydrocarbon groups having 3 to 12 carbons, for example, 3 to 8 carbons, and, for example, 3 to 6 carbons. $C_x$cyclyl and $C_x$-$C_y$cylcyl are typically used where X and Y indicate the number of carbon atoms in the ring system. The cycloalkyl group additionally can be optionally substituted, e.g., with 1, 2, 3, or 4 substituents. $C_3$-$C_{10}$cyclyl includes cyclopropyl, cyclobutyl, cyclopentyl, cyclohexyl, cyclohexenyl, 2,5-cyclohexadienyl, cycloheptyl, cyclooctyl, bicyclo[2.2.2]octyl, adamantan-1-yl, decahydronaphthyl, oxocyclohexyl, dioxocyclohexyl, thiocyclohexyl, 2-oxobicyclo [2.2.1]hept-1-yl, and the like.

Aryl and heteroaryls can be optionally substituted with one or more substituents at one or more positions, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF3, —CN, or the like.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). $C_x$heterocyclyl and $C_x$-$C_y$heterocyclyl are typically used where X and Y indicate the number of carbon atoms in the ring system. In some embodiments, 1, 2 or 3 hydrogen atoms of each ring can be substituted by a substituent. Exemplary heterocyclyl groups include, but are not limited to piperazinyl, pyrrolidinyl, dioxanyl, morpholinyl, tetrahydrofuranyl, piperidyl, 4-morpholyl, 4-piperazinyl, pyrrolidinyl, perhydropyrrolizinyl, 1,4-diazaperhydroepinyl, 1,3-dioxanyl, 1,4-dioxanyl and the like.

The terms "bicyclic" and "tricyclic" refers to fused, bridged, or joined by a single bond polycyclic ring assemblies.

The term "cyclylalkylene" means a divalent aryl, heteroaryl, cyclyl, or heterocyclyl.

As used herein, the term "fused ring" refers to a ring that is bonded to another ring to form a compound having a bicyclic structure when the ring atoms that are common to both rings are directly bound to each other. Non-exclusive examples of common fused rings include decalin, naphthalene, anthracene, phenanthrene, indole, furan, benzofuran, quinoline, and the like. Compounds having fused ring systems can be saturated, partially saturated, cyclyl, heterocyclyl, aromatics, heteroaromatics, and the like.

As used herein, the term "carbonyl" means the radical —C(O)—. It is noted that the carbonyl radical can be further substituted with a variety of substituents to form different carbonyl groups including acids, acid halides, amides, esters, ketones, and the like.

The term "carboxy" means the radical —C(O)O—. It is noted that compounds described herein containing carboxy moieties can include protected derivatives thereof, i.e., where the oxygen is substituted with a protecting group. Suitable protecting groups for carboxy moieties include benzyl, tert-butyl, and the like. The term "carboxyl" means —COOH The term "cyano" means the radical —CN.

The term, "heteroatom" refers to an atom that is not a carbon atom. Particular examples of heteroatoms include, but are not limited to nitrogen, oxygen, sulfur and halogens. A "heteroatom moiety" includes a moiety where the atom by which the moiety is attached is not a carbon. Examples of heteroatom moieties include —N=, —NR$^N$—, —N$^+$(O$^-$)=, —O—, —S— or —S(O)$_2$—, —OS(O)$_2$—, and —SS—, wherein R$^N$ is H or a further substituent.

The term "hydroxy" means the radical —OH.

The term "imine derivative" means a derivative comprising the moiety —C(NR)—, wherein R comprises a hydrogen or carbon atom alpha to the nitrogen.

The term "nitro" means the radical —NO$_2$.

An "oxaaliphatic," "oxaalicyclic", or "oxaaromatic" mean an aliphatic, alicyclic, or aromatic, as defined herein, except where one or more oxygen atoms (—O—) are positioned between carbon atoms of the aliphatic, alicyclic, or aromatic respectively.

An "oxoaliphatic," "oxoalicyclic", or "oxoaromatic" means an aliphatic, alicyclic, or aromatic, as defined herein, substituted with a carbonyl group. The carbonyl group can be an aldehyde, ketone, ester, amide, acid, or acid halide.

As used herein, the term, "aromatic" means a moiety wherein the constituent atoms make up an unsaturated ring system, all atoms in the ring system are sp$^2$ hybridized and the total number of pi electrons is equal to 4n+2. An aromatic ring can be such that the ring atoms are only carbon atoms (e.g., aryl) or can include carbon and non-carbon atoms (e.g., heteroaryl).

As used herein, the term "substituted" refers to independent replacement of one or more (typically 1, 2, 3, 4, or 5) of the hydrogen atoms on the substituted moiety with substituents independently selected from the group of substituents listed below in the definition for "substituents" or otherwise specified. In general, a non-hydrogen substituent can be any substituent that can be bound to an atom of the given moiety that is specified to be substituted. Examples of substituents include, but are not limited to, acyl, acylamino, acyloxy, aldehyde, alicyclic, aliphatic, alkanesulfonamido, alkanesulfonyl, alkaryl, alkenyl, alkoxy, alkoxycarbonyl, alkyl, alkylamino, alkylcarbanoyl, alkylene, alkylidene, alkylthios, alkynyl, amide, amido, amino, amino, aminoalkyl, aralkyl, aralkylsulfonamido, arenesulfonamido, arenesulfonyl, aromatic, aryl, arylamino, arylcarbanoyl, aryloxy, azido, carbamoyl, carbonyl, carbonyls (including ketones, carboxy, carboxylates, CF$_3$, cyano (CN), cycloalkyl, cycloalkylene, ester, ether, haloalkyl, halogen, halogen, heteroaryl, heterocyclyl, hydroxy, hydroxy, hydroxyalkyl, imino, iminoketone, ketone, mercapto, nitro, oxaalkyl, oxo, oxoalkyl, phosphoryl (including phosphonate and phosphinate), silyl groups, sulfonamide, sulfonyl (including sulfate, sulfamoyl and sulfonate), thiols, and ureido moieties, each of which may optionally also be substituted or unsubstituted. In some cases, two substituents, together with the carbon(s) to which they are attached to, can form a ring.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy, n-propyloxy, isopropyloxy, n-butyloxy, iso-butyloxy, and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. Aroxy can be represented by —O-aryl or O-heteroaryl, wherein aryl and heteroaryl are as defined below. The alkoxy and aroxy groups can be substituted as described above for alkyl.

The term "aralkyl", as used herein, refers to an alkyl group substituted with an aryl group (e.g., an aromatic or heteroaromatic group).

The term "alkylthio" refers to an alkyl group, as defined above, having a sulfur radical attached thereto. In preferred embodiments, the "alkylthio" moiety is represented by one of —S-alkyl, —S-alkenyl, and —S-alkynyl. Representative alkylthio groups include methylthio, ethylthio, and the like. The term "alkylthio" also encompasses cycloalkyl groups, alkene and cycloalkene groups, and alkyne groups. "Arylthio" refers to aryl or heteroaryl groups.

The term "sulfinyl" means the radical —SO—. It is noted that the sulfinyl radical can be further substituted with a variety of substituents to form different sulfinyl groups including sulfinic acids, sulfinamides, sulfinyl esters, sulfoxides, and the like.

The term "sulfonyl" means the radical —SO$_2$—. It is noted that the sulfonyl radical can be further substituted with a variety of substituents to form different sulfonyl groups including sulfonic acids (—SO$_3$H), sulfonamides, sulfonate esters, sulfones, and the like.

The term "thiocarbonyl" means the radical —C(S)—. It is noted that the thiocarbonyl radical can be further substituted with a variety of substituents to form different thiocarbonyl groups including thioacids, thioamides, thioesters, thioketones, and the like.

As used herein, the term "amino" means —NH$_2$. The term "alkylamino" means a nitrogen moiety having at least one straight or branched unsaturated aliphatic, cyclyl, or heterocyclyl radicals attached to the nitrogen. For example, representative amino groups include —NH$_2$, —NHCH$_3$, —N(CH$_3$)$_2$, —NH(C$_1$-C$_{10}$alkyl), —N(C$_1$-C$_{10}$alkyl)$_2$, and the like. The term "alkylamino" includes "alkenylamino," "alkynylamino," "cyclylamino," and "heterocyclylamino." The term "arylamino" means a nitrogen moiety having at least one aryl radical attached to the nitrogen. For example NHaryl, and —N(aryl)$_2$. The term "heteroarylamino" means a nitrogen moiety having at least one heteroaryl radical attached to the nitrogen. For example —NHheteroaryl, and —N(heteroaryl)$_2$. Optionally, two substituents together with the nitrogen can also form a ring. Unless indicated otherwise, the compounds described herein containing amino moieties can include protected derivatives thereof. Suitable protecting groups for amino moieties include acetyl, tertbutoxycarbonyl, benzyloxycarbonyl, and the like.

The term "aminoalkyl" means an alkyl, alkenyl, and alkynyl as defined above, except where one or more substituted or unsubstituted nitrogen atoms (—N—) are positioned between carbon atoms of the alkyl, alkenyl, or alkynyl. For example, an (C$_2$-C$_6$) aminoalkyl refers to a chain comprising between 2 and 6 carbons and one or more nitrogen atoms positioned between the carbon atoms.

The term "alkoxyalkoxy" means —O-(alkyl)-O-(alkyl), such as —OCH$_2$CH$_2$OCH$_3$, and the like.

The term "alkoxycarbonyl" means —C(O)O-(alkyl), such as —C(=O)OCH$_3$, —C(=O)OCH$_2$CH$_3$, and the like.

The term "alkoxyalkyl" means -(alkyl)-O-(alkyl), such as —CH$_2$OCH$_3$, —CH$_2$OCH$_2$CH$_3$, and the like.

The term "aryloxy" means —O-(aryl), such as —O-phenyl, —O-pyridinyl, and the like.

The term "arylalkyl" means -(alkyl)-(aryl), such as benzyl (i.e., —CH$_2$phenyl), —CH$_2$-pyrindinyl, and the like.

The term "arylalkyloxy" means —O-(alkyl)-(aryl), such as —O-benzyl, —O—CH$_2$-pyridinyl, and the like.

The term "cycloalkyloxy" means —O-(cycloalkyl), such as —O-cyclohexyl, and the like.

The term "cycloalkylalkyloxy" means —O-(alkyl)-(cycloalkyl), such as —OCH$_2$cyclohexyl, and the like.

The term "aminoalkoxy" means —O-(alkyl)-NH$_2$, such as —OCH$_2$NH$_2$, —OCH$_2$CH$_2$NH$_2$, and the like.

The term "mono- or di-alkylamino" means —NH(alkyl) or —N(alkyl)(alkyl), respectively, such as —NHCH$_3$, —N(CH$_3$)$_2$, and the like.

The term "mono- or di-alkylaminoalkoxy" means —O-(alkyl)-NH(alkyl) or —O-(alkyl)-N(alkyl)(alkyl), respectively, such as —OCH$_2$NHCH$_3$, —OCH$_2$CH$_2$N(CH$_3$)$_2$, and the like.

The term "arylamino" means —NH(aryl), such as —NH-phenyl, —NH-pyridinyl, and the like.

The term "arylalkylamino" means —NH-(alkyl)-(aryl), such as —NH-benzyl, —NHCH$_2$-pyridinyl, and the like.

The term "alkylamino" means —NH(alkyl), such as —NHCH$_3$, —NHCH$_2$CH$_3$, and the like.

The term "cycloalkylamino" means —NH-(cycloalkyl), such as —NH-cyclohexyl, and the like.

The term "cycloalkylalkylamino" —NH-(alkyl)-(cycloalkyl), such as —NHCH$_2$— cyclohexyl, and the like.

It is noted in regard to all of the definitions provided herein that the definitions should be interpreted as being open ended in the sense that further substituents beyond those specified may be included. Hence, a C$_1$ alkyl indicates that there is one carbon atom but does not indicate what are the substituents on the carbon atom. Hence, a C$_1$ alkyl comprises methyl (i.e., —CH3) as well as CR$_a$R$_b$R$_c$ where R$_a$, R$_b$, and R$_c$ can each independently be hydrogen or any other substituent where the atom alpha to the carbon is a heteroatom or cyano. Hence, CF$_3$, CH$_2$OH and CH$_2$CN are all C$_1$ alkyls.

Unless otherwise stated, structures depicted herein are meant to include compounds which differ only in the presence of one or more isotopically enriched atoms. For example, compounds having the present structure except for the replacement of a hydrogen atom by a deuterium or tritium, or the replacement of a carbon atom by a $^{13}$C- or $^{14}$C-enriched carbon are within the scope of the invention.

A "pharmaceutically acceptable salt", as used herein, is intended to encompass any compound described herein that is utilized in the form of a salt thereof, especially where the salt confers on the compound improved pharmacokinetic properties as compared to the free form of compound or a different salt form of the compound. The pharmaceutically acceptable salt form can also initially confer desirable pharmacokinetic properties on the compound that it did not previously possess, and may even positively affect the pharmacodynamics of the compound with respect to its therapeutic activity in the body. An example of a pharmacokinetic property that can be favorably affected is the manner in which the compound is transported across cell membranes, which in turn may directly and positively affect the absorption, distribution, biotransformation and excretion of the compound. While the route of administration of the pharmaceutical composition is important, and various anatomical, physiological and pathological factors can critically affect bioavailability, the solubility of the compound is usually dependent upon the character of the particular salt form thereof, which it utilized. One of skill in the art will appreciate that an aqueous solution of the compound will provide the most rapid absorption of the compound into the body of a subject being treated, while lipid solutions and suspensions, as well as solid dosage forms, will result in less rapid absorption of the compound.

Pharmaceutically acceptable salts include those derived from inorganic acids such as sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. See, for example, Berge et al., "Pharmaceutical Salts", *J. Pharm. Sci.* 66:1-19 (1977), the content of which is herein incorporated by reference in its entirety. Exemplary salts also include the hydrobromide, hydrochloride, sulfate, bisulfate, phosphate, nitrate, acetate, succinate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. Suitable acids which are capable of forming salts with the compounds of the disclosure include inorganic acids such as hydrochloric acid, hydrobromic acid, perchloric acid, nitric acid, thiocyanic acid, sulfuric acid, phosphoric acid, and the like; and organic acids such as 1,2-ethanedisulfonic acid, 2-hydroxyethanesulfonic acid, 2-naphthalenesulfonic acid, 3-phenylpropionic acid, 4-methylbicyclo[2.2.2]oct-2-ene-1-carboxylic acid, 4,4'-mefhylenebis(3-hydroxy-2-ene-1-carboxylic acid), acetic acid, anthranilic acid, benzenesulfonic acid, benzoic acid, camphorsulfonic acid, cinnamic acid, citric acid, cyclopentanepropionic acid, ethanesulfonic acid, formic acid, fumaric acid, glucoheptonic acid, gluconic acid, glutamic acid, glycolic acid, heptanoic acid, hydroxynaphthoic acid, lactic acid, lauryl sulfuric acid, maleic acid, malic acid, malonic acid, mandelic acid, methanesulfonic acid, muconic acid, naphthalene sulfonic acid, o-(4-hydroxybenzoyl)benzoic acid, oxalic acid, p-chlorobenzenesulfonic acid, propionic acid, p-toluenesulfonic acid, pyruvic acid, salicylic acid, stearic acid, succinic acid, sulfanilic acid, tartaric acid, tertiary butylacetic acid, trifluoroacetic acid, trimethylacetic acid, and the like. Suitable bases capable of forming salts with the compounds of the disclosure include inorganic bases such as sodium hydroxide, ammonium hydroxide, sodium carbonate, calcium hydroxide, potassium hydroxide and the like; and organic bases such as mono-, di- and tri-alkyl and aryl amines (e.g., triethylamine, diisopropyl amine, methyl amine, dimethyl amine, N-methylglucamine, pyridine, picoline, dicyclohexylamine, N,N'-dibezylethylenediamine, and the like), and optionally substituted ethanol-amines (e.g., ethanolamine, diethanolamine, trierhanolamine and the like).

In some embodiments, the compounds described herein can be in the form of a prodrug. The term "prodrug" as used herein refers to compounds that can be converted via some chemical or physiological process (e.g., enzymatic processes and metabolic hydrolysis) to compound described herein. Thus, the term "prodrug" also refers to a precursor of a biologically active compound that is pharmaceutically acceptable. A prodrug can be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. For example, a compound comprising a hydroxy group can be administered as an ester that is converted by hydrolysis in vivo to the hydroxy compound. Suitable esters that can be converted in vivo into hydroxy compounds include acetates, citrates, lactates, tartrates, malonates, oxalates, salicylates, propionates, succinates, fumarates, formates, benzoates, maleates, methylene-bis-b-hydroxynaphthoates, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group can be administered as an amide, e.g., acetamide, formamide and benzamide that is converted by hydrolysis in vivo to the amine compound. See Harper, "Drug Latentiation" in Jucker, ed. *Progress in Drug Research* 4:221-294 (1962); Morozowich et al, "Application of Physical Organic Principles to Prodrug Design" in E. B. Roche ed. *Design of Biopharmaceutical Properties through Prodrugs and Analogs*, APHA Acad. Pharm. Sci. 40 (1977); *Bioreversible Carriers in Drug in Drug Design, Theory and Application*, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design.* 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics," *Pharm. Biotech.* 11:345-365; Gaignault et al. (1996) "Designing Prodrugs and Bioprecursors I. Carrier Prodrugs," *Pract. Med. Chem.* 671-696; Asgharnejad, "Improving Oral Drug Transport", in Transport Processes in Pharmaceutical Systems, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Pharmacokinet.*, 15(2): 143-53 (1990); Balimane and Sinko, "Involvement of multiple transporters in the oral absorption of nucleoside analogues", *Adv. Drug Delivery Rev.*, 39(1-3): 183-209 (1999); Browne, "Fosphenytoin (Cerebyx)", *Clin. Neuropharmacol.* 20(1): 1-12 (1997); Bundgaard, "Bioreversible derivatization of drugS—principle and applicability to improve the therapeutic effects of drugs", *Arch. Pharm. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs", Arfv. *Drug Delivery Rev.* 8(1): 1-38 (1992); Fleisher et al. "Improved oral drug delivery: solubility limitations overcome by the use of prodrugs", Arfv. *Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *Pharm. Sci.*, 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," *Chem. Soc., Chem. Commun.*, 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J. Pharm. Sci.* 4: 49-59 (1996); Gangwar et al., "Pro-drug, molecular structure and percutaneous delivery", *Des. Biopharm. Prop. Prodrugs Analogs*, [*Symp.*]Meeting Date 1976, 409-21. (1977); Nathwani and Wood, "Penicillins: a current review of their clinical pharmacology and therapeutic use", *Drugs*

45(6): 866-94 (1993); Sinhababu and Thakker, "Prodrugs of anticancer agents", *Adv. Drug Delivery Rev.* 19(2): 241-273 (1996); Stella et al., "Prodrugs. Do they have advantages in clinical practice?", *Drugs* 29(5): 455-73 (1985); Tan et al. "Development and optimization of anti-HIV nucleoside analogs and prodrugs: A review of their cellular pharmacology, structure-activity relationships and pharmacokinetics", *Adv. Drug Delivery Rev.* 39(1-3): 117-151 (1999); Taylor, "Improved passive oral drug delivery via prodrugs", *Adv. Drug Delivery Rev.*, 19(2): 131-148 (1996); Valentino and Borchardt, "Prodrug strategies to enhance the intestinal absorption of peptides", *Drug Discovery Today* 2(4): 148-155 (1997); Wiebe and Knaus, "Concepts for the design of anti-HIV nucleoside prodrugs for treating cephalic HIV infection", *Adv. Drug Delivery Rev.*: 39(1-3):63-80 (1999); Waller et al., "Prodrugs", *Br. J. Clin. Pharmac.* 28: 497-507 (1989), content of all of which are herein incorporated by reference in its entirety.

The term "protected derivatives" means derivatives of compounds described herein in which a reactive site or sites are blocked with protecting groups. Protected derivatives are useful in the preparation of compounds or in themselves can be active. A comprehensive list of suitable protecting groups can be found in T. W. Greene, *Protecting Groups in Organic Synthesis,* 3rd edition, John Wiley & Sons, Inc. 1999.

"Isomers" mean any compound having identical molecular formulae but differing in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are nonsuperimposable mirror images are termed "enantiomers" or sometimes "optical isomers". A carbon atom bonded to four nonidentical substituents is termed a "chiral center". A compound with one chiral center has two enantiomeric forms of opposite chirality. A mixture of the two enantiomeric forms is termed a "racemic mixture". A compound that has more than one chiral center has $2^{n-1}$ enantiomeric pairs, where n is the number of chiral centers. Compounds with more than one chiral center may exist as ether an individual diastereomers or as a mixture of diastereomers, termed a "diastereomeric mixture". When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992).

The term "enantiomer" is used to describe one of a pair of molecular isomers which are mirror images of each other and non-superimposable. Other terms used to designate or refer to enantiomers include "stereoisomers" (because of the different arrangement or stereochemistry around the chiral center; although all enantiomers are stereoisomers, not all stereoisomers are enantiomers) or "optical isomers" (because of the optical activity of pure enantiomers, which is the ability of different pure enantiomers to rotate plane polarized light in different directions). Enantiomers generally have identical physical properties, such as melting points and boiling points, and also have identical spectroscopic properties. Enantiomers can differ from each other with respect to their interaction with plane-polarized light and with respect to biological activity.

The designations "R" and "S" are used to denote the absolute configuration of the molecule about its chiral center(s). The designations may appear as a prefix or as a suffix; they may or may not be separated from the isomer by a hyphen; they may or may not be hyphenated; and they may or may not be surrounded by parentheses.

The designations or prefixes "(+)" and "(−)" are employed to designate the sign of rotation of plane-polarized light by the compound, with (−) meaning that the compound is levorotatory (rotates to the left). A compound prefixed with (+) is dextrorotatory (rotates to the right).

The term "racemic mixture," "racemic compound" or "racemate" refers to a mixture of the two enantiomers of one compound. An ideal racemic mixture is one wherein there is a 50:50 mixture of both enantiomers of a compound such that the optical rotation of the (+) enantiomer cancels out the optical rotation of the (−) enantiomer.

The term "resolving" or "resolution" when used in reference to a racemic mixture refers to the separation of a racemate into its two enantiomorphic forms (i.e., (+) and (−); (R) and (S) forms). The terms can also refer to enantioselective conversion of one isomer of a racemate to a product.

The term "enantiomeric excess" or "ee" refers to a reaction product wherein one enantiomer is produced in excess of the other, and is defined for a mixture of (+)- and (−)-enantiomers, with composition given as the mole or weight or volume fraction F(+) and F(−) (where the sum of F(+) and F(−)=1). The enantiomeric excess is defined as *F(+)−F(−)* and the percent enantiomeric excess by 100× *F(+)−F(−)*. The "purity" of an enantiomer is described by its ee or percent ee value (% ee).

Whether expressed as a "purified enantiomer" or a "pure enantiomer" or a "resolved enantiomer" or "a compound in enantiomeric excess", the terms are meant to indicate that the amount of one enantiomer exceeds the amount of the other. Thus, when referring to an enantiomer preparation, both (or either) of the percent of the major enantiomer (e.g. by mole or by weight or by volume) and (or) the percent enantiomeric excess of the major enantiomer may be used to determine whether the preparation represents a purified enantiomer preparation.

The term "enantiomeric purity" or "enantiomer purity" of an isomer refers to a qualitative or quantitative measure of the purified enantiomer; typically, the measurement is expressed on the basis of ee or enantiomeric excess.

The terms "substantially purified enantiomer," "substantially resolved enantiomer" "substantially purified enantiomer preparation" are meant to indicate a preparation (e.g. derived from non-optically active starting material, substrate, or intermediate) wherein one enantiomer has been enriched over the other, and more preferably, wherein the other enantiomer represents less than 20%, more preferably less than 10%, and more preferably less than 5%, and still more preferably, less than 2% of the enantiomer or enantiomer preparation.

The terms "purified enantiomer," "resolved enantiomer" and "purified enantiomer preparation" are meant to indicate a preparation (e.g. derived from non-optically active starting material, substrates or intermediates) wherein one enantiomer (for example, the R-enantiomer) is enriched over the other, and more preferably, wherein the other enantiomer (for example the S-enantiomer) represents less than 30%, preferably less than 20%, more preferably less than 10% (e.g. in this particular instance, the R-enantiomer is substantially free of the S-enantiomer), and more preferably less than 5% and still more preferably, less than 2% of the preparation. A purified enantiomer may be synthesized substantially free of the other enantiomer, or a purified enantiomer may be synthesized in a stereo-preferred procedure, followed by separation steps, or a purified enantiomer may be derived from a racemic mixture.

The term "enantioselectivity," also called the enantiomeric ratio indicated by the symbol "E," refers to the selective capacity of an enzyme to generate from a racemic substrate one enantiomer relative to the other in a product racemic mixture; in other words, it is a measure of the ability of the enzyme to distinguish between enantiomers. A non-selective reaction has an E of 1, while resolutions with E's above 20 are generally considered useful for synthesis or resolution. The enantioselectivity resides in a difference in conversion rates between the enantiomers in question. Reaction products are obtained that are enriched in one of the enantiomers; conversely, remaining substrates are enriched in the other enantiomer. For practical purposes it is generally desirable for one of the enantiomers to be obtained in large excess. This is achieved by terminating the conversion process at a certain degree of conversion.

The disclosure is further illustrated by the following examples which should not be construed as limiting. The examples are illustrative only, and are not intended to limit, in any manner, any of the aspects described herein. The following examples do not in any way limit the invention.

Examples

Over 200,000 patients are likely to be diagnosed with breast cancer in the United States (Jemal et al., *Global cancer statistics*. CA Cancer J Clin., 2011, 61(2): p. 69-90). Although triple-negative and basal-like tumors account for about 15% of all invasive breast cancers, it disproportionally occurs in young Black and Hispanic women. Also, women carrying a mutation in BRCA1 show both phenotypes. So far, anti-EGFR therapeutic has proven to be ineffective in treating the triple-negative breast cancer. Lately, Poly-ADP ribose polymerase (PARP) inhibitors have proven to be ineffective in a recent clinical trial (Guha, M., *PARP inhibitors stumble in breast cancer*. Nat Biotechnol., 2011, 29(5): p. 373-4).

NF-κB is constitutively activated in several cancers including breast cancer and plays an important role in cancer cells survival (Nakshatri et al., *Constitutive activation of NF-kappaB during progression of breast cancer to hormone-independent growth*. Mol Cell Biol., 1997, 17(7): p. 3629-39 and Pratt et al., *The canonical NF-kappaB pathway is required for formation of luminal mammary neoplasias and is activated in the mammary progenitor population*. Oncogene, 2009, 28(30): p. 2710-22). Activation of NF-KB, a common molecular event that stems from a variety of stimuli from inflammation, overexpression of growth factor receptors and metabolic dysfunction, is critical for tumor survival (Schmitz et al., *NF-KB: A Multifaceted Transcription Factor Regulated at Several Levels*. ChemBioChem., 2004, 5(10): p. 1348-1358). Recently, breast cancer stem cells (BCSC) have been implicated in resistance, recurrence and metastasis (Al-Ejeh et al., *Breast cancer stem cells: treatment resistance and therapeutic opportunities*. Carcinogenesis, 2011, 32(5): p. 650-8). More importantly, activation of NF-KB is also critical for BCSC function (Shostak et al., *NF-kappaB, stem cells and breast cancer: the links get stronger*. Breast Cancer Res., 2011, 13(4): p. 214 and Zhou et al., *NF-kappaB pathway inhibitors preferentially inhibit breast cancer stem-like cells*, Breast Cancer Res Treat, 2011, 111(3): p. 419-27). Activation of NF-κB leads to nuclear localization of RelA/p65, which has been implicated in chemoresistance (Benezra et al., *BRCA1 augments transcription by the NF-kappaB transcription factor by binding to the Re! domain of the p65/Re/A subunit*. J Biol Chem., 2003, 278(29): p. 26333-41 and Jones et al., *Nuclear NF-kappaB/p65 expression and response to neoadjuvant chemotherapy in breast cancer*. J Clin Pathol., 2011, 64(2): p. 130-5). As shown herein, blocking RelA/p65 nuclear translocation can prevent cancer growth and metastasis.

The inventors used virtual screening to identify a small molecule, CRL1101, to block RelA function. Briefly, the three-dimensional structures of RelA dimer-DNA complexes (PBD code: 2RAM, INFI and 1VKX) were used to as template. Computational analysis was performed at different temperature and simulation times to identify critical sites to disrupt the nuclear localization signal (NLS) region located nearby at the C-terminus. Inventors have identified several chemical probes that potentially disrupt NLS signaling. The calculations were performed on Cedars-Sinai High performance computing Center facility.

In Vitro Biological Activity of RelA Inhibitor, CRL1101:
CRL1101 significantly inhibited cell proliferation (FIG. 1A), colony formation (FIG. 1B) and nuclear localization in breast cancer cells (FIG. 2).

Therapeutic Efficacy of CRL1101 in a Pre-Clinical Breast Cancer Mouse Model:
Therapeutic efficacy of CRL1101 was tested in xenograft breast cancer model. Briefly, triple-negative breast cancer cells, MDA-MB-231 were used to grow tumor in athymic mice. Mice were treated with 25 mg/kg/day, IP for 4 weeks. The control group was treated with vehicle. Mice treated with CRL1101 show significant reduction in tumor growth (FIG. 3).

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

What is claimed is:
1. A method for treating a cancer or a cancerous condition or a tumor, the method comprising administering to a subject having a cancer or cancerous condition a therapeutically effective amount of a compound, wherein the compound is

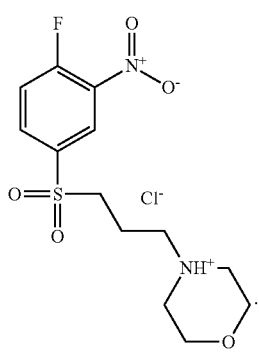 [SMILES: O=[N+]([O-])c1cc(S(=O)(=O)CCC[NH+]2CCOCC2)ccc1F ; [Cl-]]

2. The method of claim 1, wherein the compound modulates a RelA activity or function.

3. The method of claim 1, further comprising the step of selecting the subject having a cancer, a cancerous condition; or a tumor.

4. The method of claim 3, wherein the cancer is a breast cancer, squamous cell cancer, lung cancer, a cancer of the peritoneum, a hepatocellular cancer, a gastric cancer, a pancreatic cancer, a glioblastoma, a cervical cancer, an ovarian cancer, a liver cancer, a bladder cancer, a hepatoma, a colon cancer, a colorectal cancer, an endometrial or uterine carcinoma, a salivary gland carcinoma, a kidney or renal cancer, a prostate cancer, a vulval cancer, a thyroid cancer, a head and neck cancer, a B-cell lymphoma, a chronic lymphocytic leukemia (CLL); an acute lymphoblastic leukemia (ALL), a Hairy cell leukemia, or a chronic myeloblasts leukemia.

5. The method of claim 4, wherein the cancer is a breast cancer.

6. The method of claim 5, wherein the cancer is a triple negative breast cancer.

7. The method of claim 1, further comprising administering one or more additional anti-cancer therapies.

8. The method of claim 7, wherein the additional anti-cancer therapy comprises surgery, radiation therapy, biotherapy, immunotherapy, or chemotherapy.

9. The method of claim 1, further comprising administering one or more anti-cancer therapeutic agents.

10. The method of claim 9, wherein the anti-cancer therapeutic agent is a chemotherapeutic agent, a growth inhibitor agent, an anti-angiogenesis agent, a cytotoxic agent, an anti-hormonal agent, or a cytokine.

11. The method of claim 1, wherein the compound is formulated in a pharmaceutical composition comprising the compound and a pharmaceutically acceptable excipient or carrier.

12. The method of claim 1, wherein the compound is formulated in a nanoparticle.

13. The method of claim 12, wherein the nanoparticle is formulated in a pharmaceutical composition comprising the nanoparticle and a pharmaceutically acceptable excipient or carrier.

* * * * *